(12) United States Patent
Howard et al.

(10) Patent No.: US 10,051,910 B2
(45) Date of Patent: *Aug. 21, 2018

(54) METHOD, SYSTEM AND DEVICE FOR MONITORING PROTECTIVE HEADGEAR

(71) Applicant: THL Holding Company, LLC, Round Rock, TX (US)

(72) Inventors: John W. Howard, Cedar Park, TX (US); Richard Cutler, Leander, TX (US)

(73) Assignee: THL HOLDING COMPANY, LLC, Round Rock, TX (US)

( * ) Notice: Subject to any disclaimer, the term of this patent is extended or adjusted under 35 U.S.C. 154(b) by 518 days.

This patent is subject to a terminal disclaimer.

(21) Appl. No.: 14/284,262

(22) Filed: May 21, 2014

(65) Prior Publication Data

US 2014/0364772 A1 Dec. 11, 2014

Related U.S. Application Data

(63) Continuation of application No. 13/586,424, filed on Aug. 15, 2012, now Pat. No. 8,766,798, which is a continuation-in-part of application No. 12/713,316, filed on Feb. 26, 2010, now Pat. No. 8,253,559.

(60) Provisional application No. 61/558,764, filed on Nov. 11, 2011, provisional application No. 61/623,189, filed on Apr. 12, 2012.

(51) Int. Cl.
| *A42B 3/30* | (2006.01) |
| *A42B 3/04* | (2006.01) |
| *A42B 3/00* | (2006.01) |
| *A42B 3/08* | (2006.01) |
| *A61B 5/00* | (2006.01) |
| *A61B 5/11* | (2006.01) |
| *A63B 71/08* | (2006.01) |

(52) U.S. Cl.
CPC .............. *A42B 3/30* (2013.01); *A42B 3/00* (2013.01); *A42B 3/046* (2013.01); *A42B 3/08* (2013.01); *A61B 5/0004* (2013.01); *A61B 5/1122* (2013.01); *A61B 5/6803* (2013.01); *A61B 5/7282* (2013.01); *A63B 71/085* (2013.01)

(58) Field of Classification Search
None
See application file for complete search history.

(56) References Cited

U.S. PATENT DOCUMENTS

| 3,448,738 A | * | 6/1969 | Berghash | A63B 71/085 128/861 |
| 4,977,905 A | * | 12/1990 | Kittelsen | A63B 71/085 128/861 |
| 5,063,940 A | * | 11/1991 | Adell | A63B 71/085 128/861 |
| 5,447,305 A | * | 9/1995 | Socci | A42B 3/0433 473/458 |

(Continued)

*Primary Examiner* — Matthew Kremer
(74) *Attorney, Agent, or Firm* — Garlick & Markison; Bruce E. Stuckman

(57) ABSTRACT

A sensor module generates sensor data in response to an impact to protective headgear, wherein the sensor module includes an accelerometer and a gyroscope and wherein the sensor data includes linear acceleration data and rotational velocity data. A device processing module generates event data in response to the sensor data. A device interface sends the event data to a monitoring device when the device interface is coupled to the monitoring device.

20 Claims, 26 Drawing Sheets

(56) References Cited

U.S. PATENT DOCUMENTS

| | | | |
|---|---|---|---|
| 5,539,935 A | 7/1996 | Rush | |
| 6,364,834 B1* | 4/2002 | Reuss | A61B 5/0205 |
| | | | 128/903 |
| 6,589,189 B2 | 7/2003 | Meyerson | |
| 6,826,509 B2 | 11/2004 | Crisco | |
| 6,941,952 B1 | 9/2005 | Rush | |
| 7,570,170 B2 | 8/2009 | Wallner | |
| 8,766,798 B2* | 7/2014 | Howard | A42B 3/046 |
| | | | 340/479 |
| 8,909,497 B1* | 12/2014 | Shkolnikov | G01P 15/00 |
| | | | 340/573.1 |
| 2002/0060247 A1* | 5/2002 | Krishnaswamy | A61B 5/0002 |
| | | | 235/472.01 |
| 2002/0176330 A1* | 11/2002 | Ramonowski | G11B 31/00 |
| | | | 369/30.36 |
| 2003/0158693 A1* | 8/2003 | Kai | A61B 5/0006 |
| | | | 702/127 |
| 2006/0015287 A1* | 1/2006 | Vock | A42B 3/046 |
| | | | 702/141 |
| 2006/0189852 A1 | 8/2006 | Greenwald | |
| 2008/0076971 A1* | 3/2008 | Clapp | A61B 5/0002 |
| | | | 600/300 |
| 2010/0083733 A1* | 4/2010 | Russell | G01P 15/0891 |
| | | | 73/12.01 |
| 2010/0120585 A1* | 5/2010 | Quy | A61B 5/6826 |
| | | | 482/8 |
| 2010/0137778 A1* | 6/2010 | Kunjan | A61B 5/1427 |
| | | | 604/6.15 |
| 2010/0312079 A1* | 12/2010 | Larsen | A61B 5/742 |
| | | | 600/323 |
| 2011/0184663 A1* | 7/2011 | Mack | A42B 3/046 |
| | | | 702/41 |

* cited by examiner

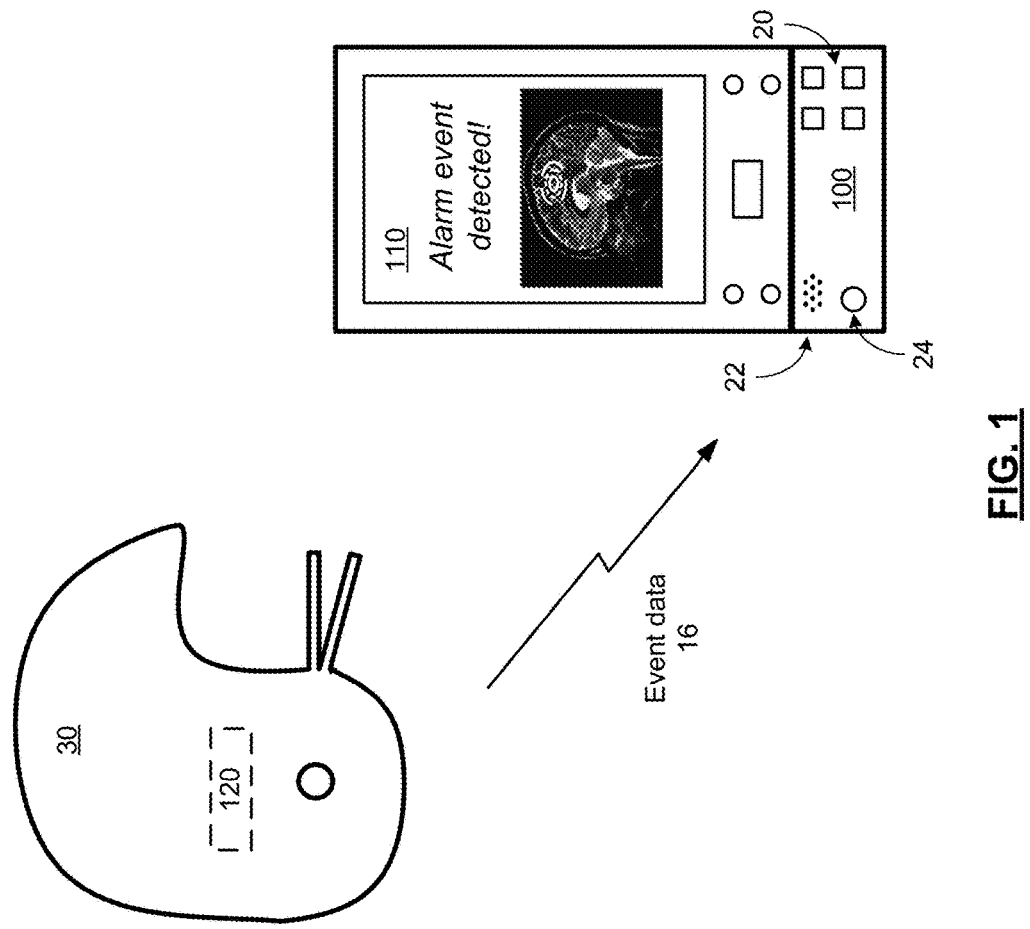

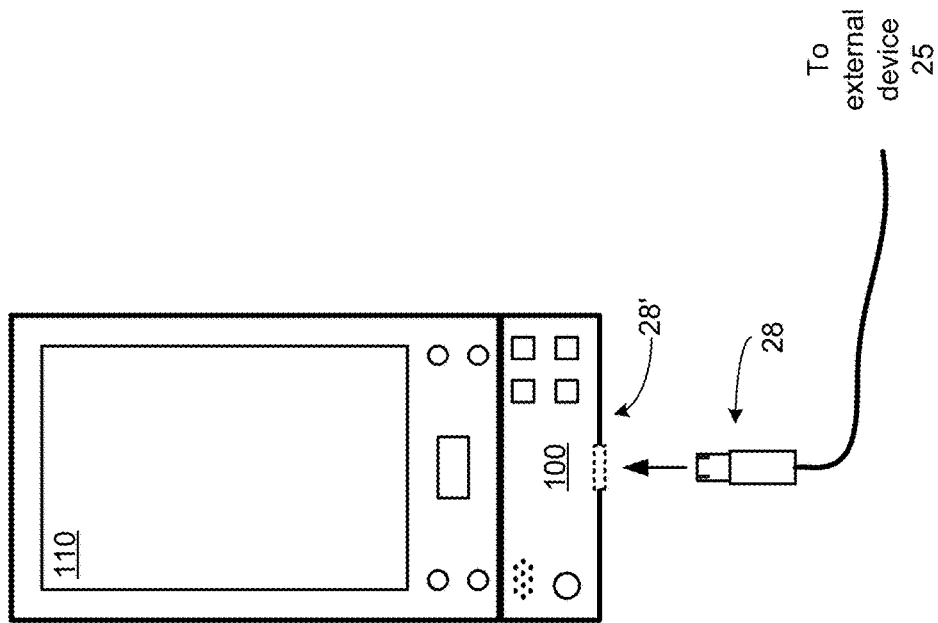
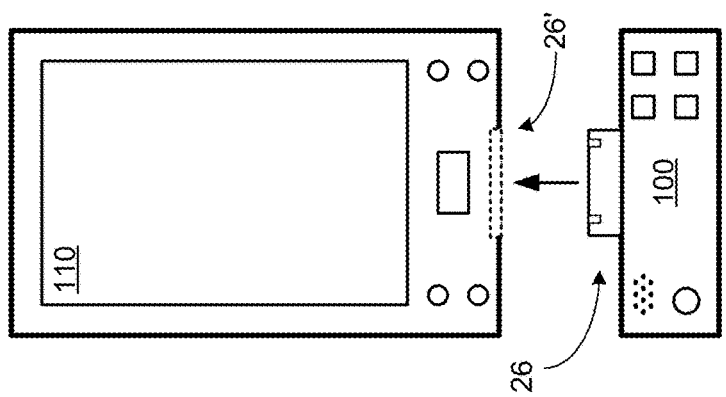

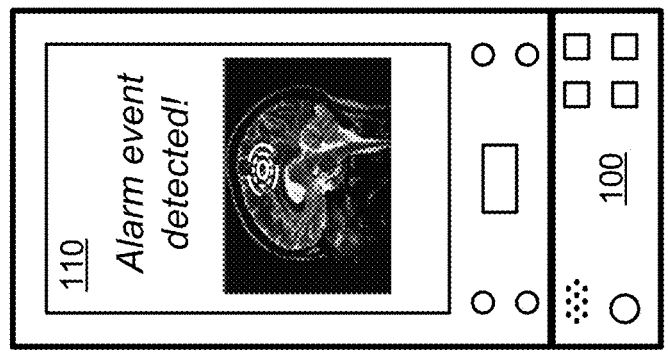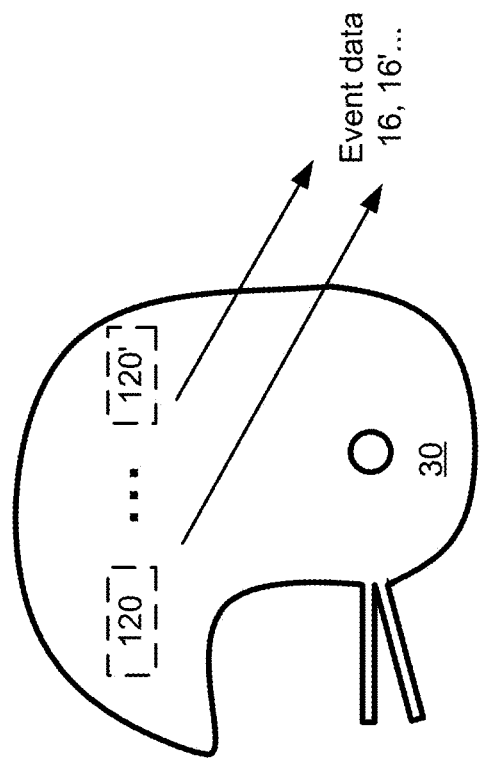
FIG. 5

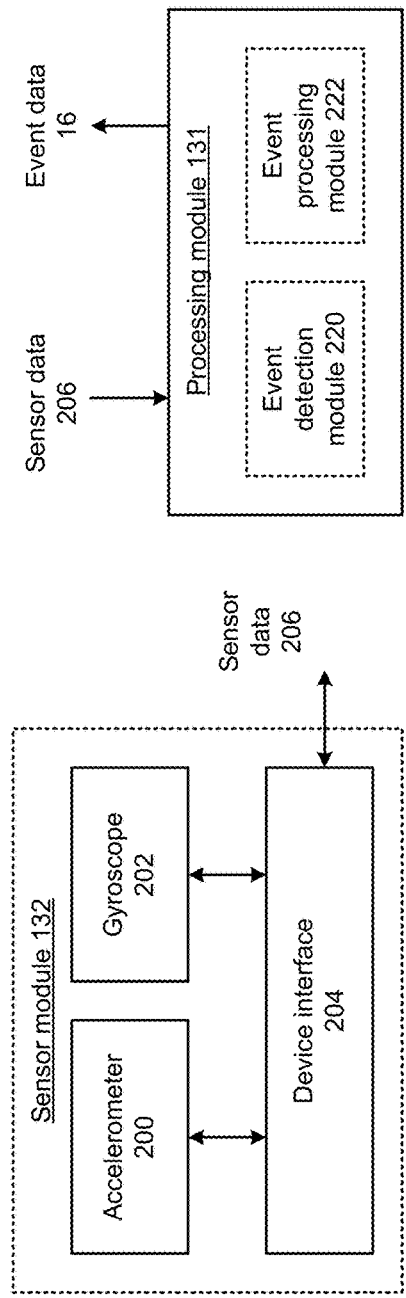
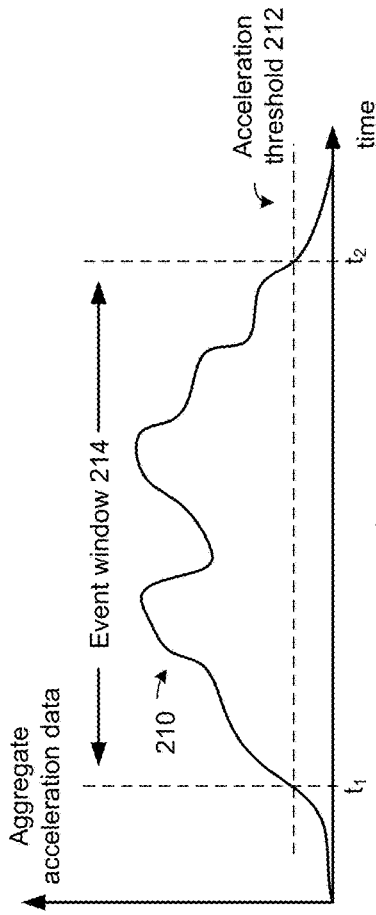
FIG. 6
FIG. 7
FIG. 8

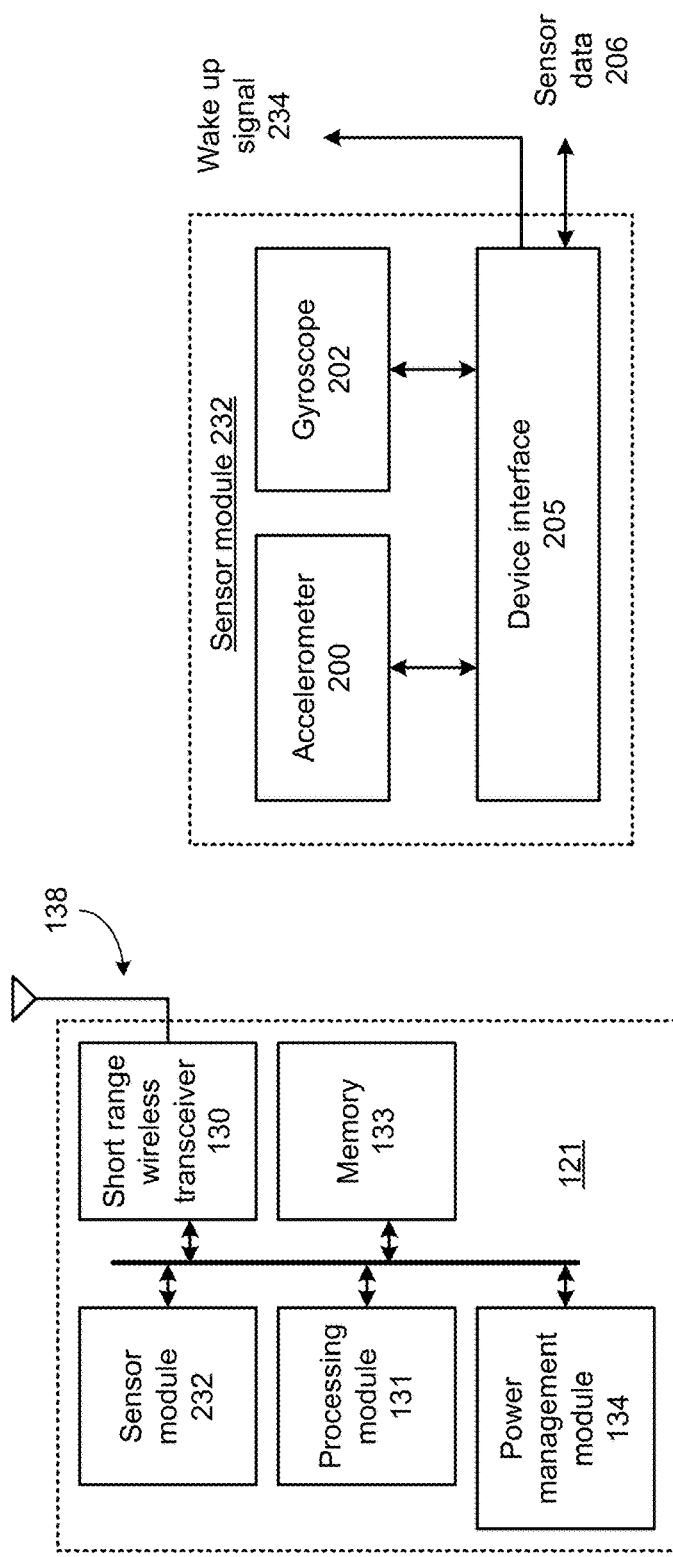

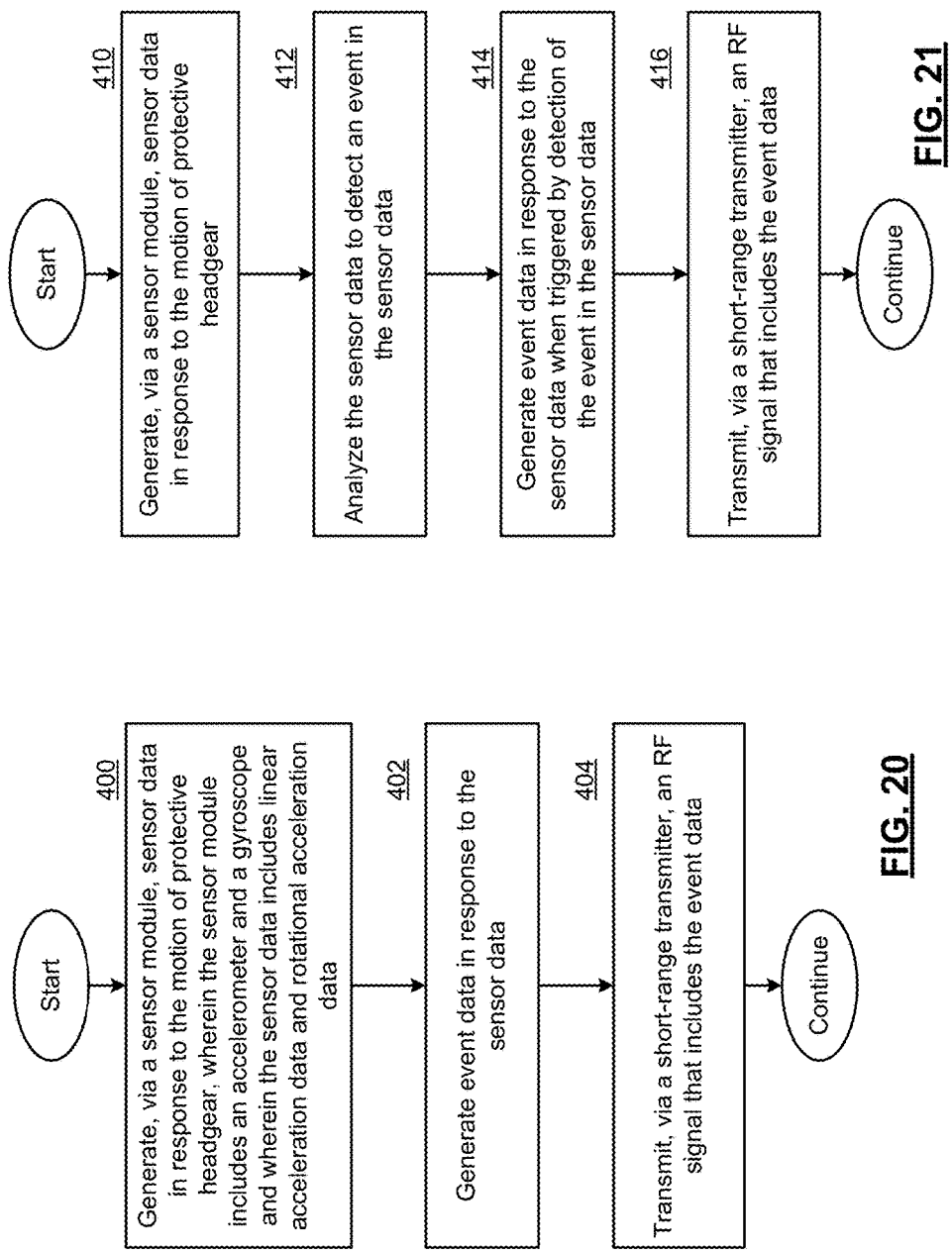

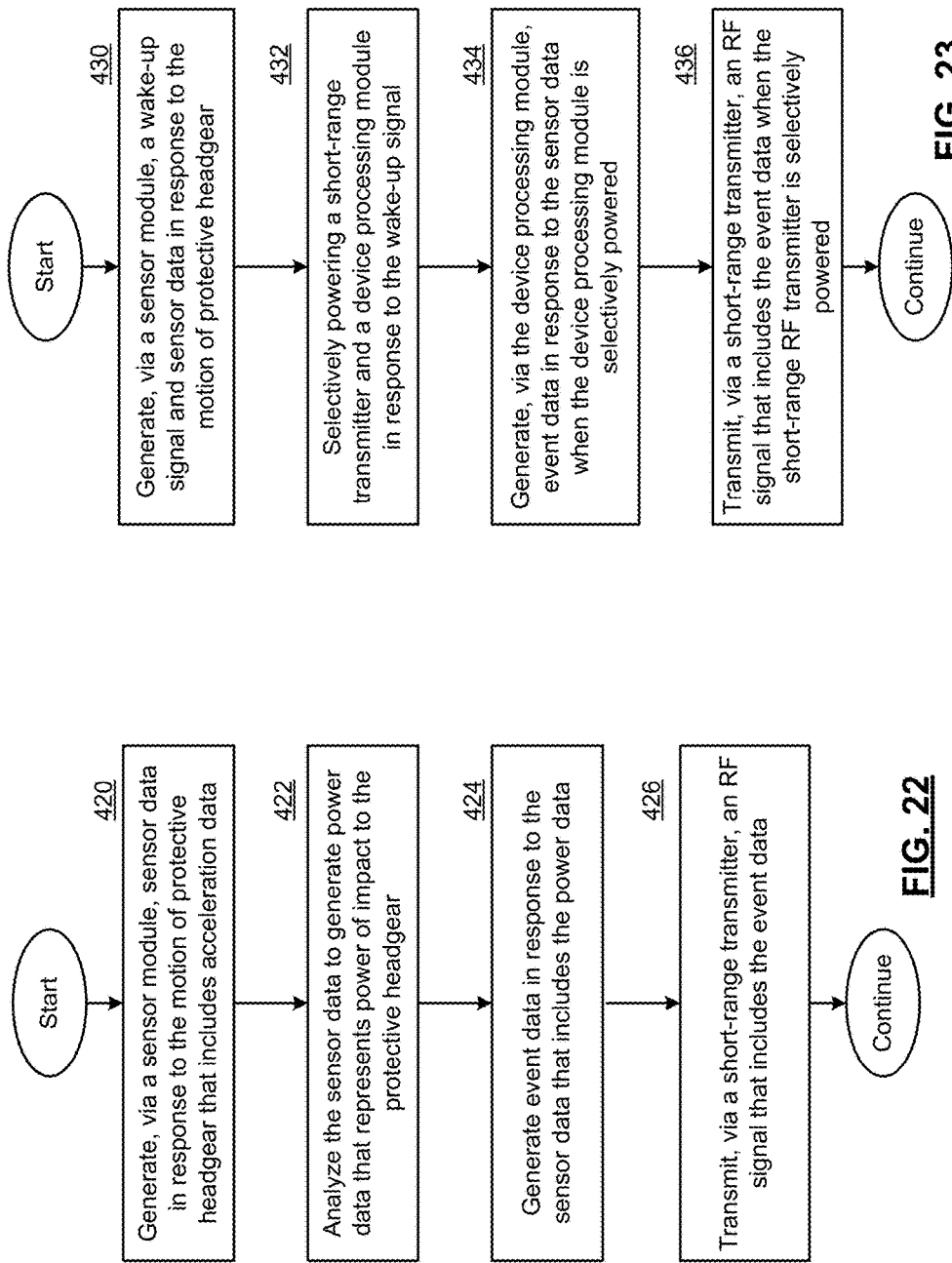

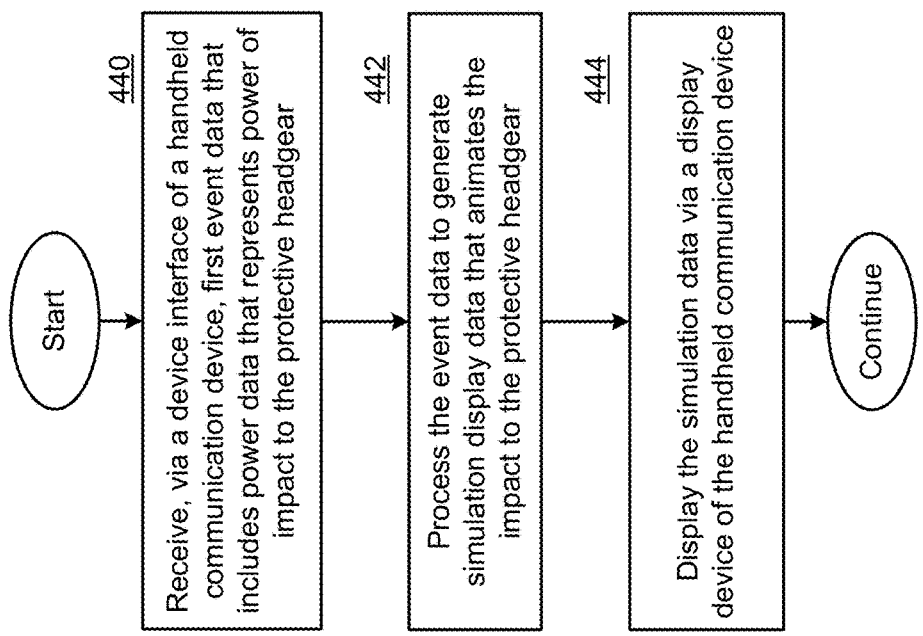

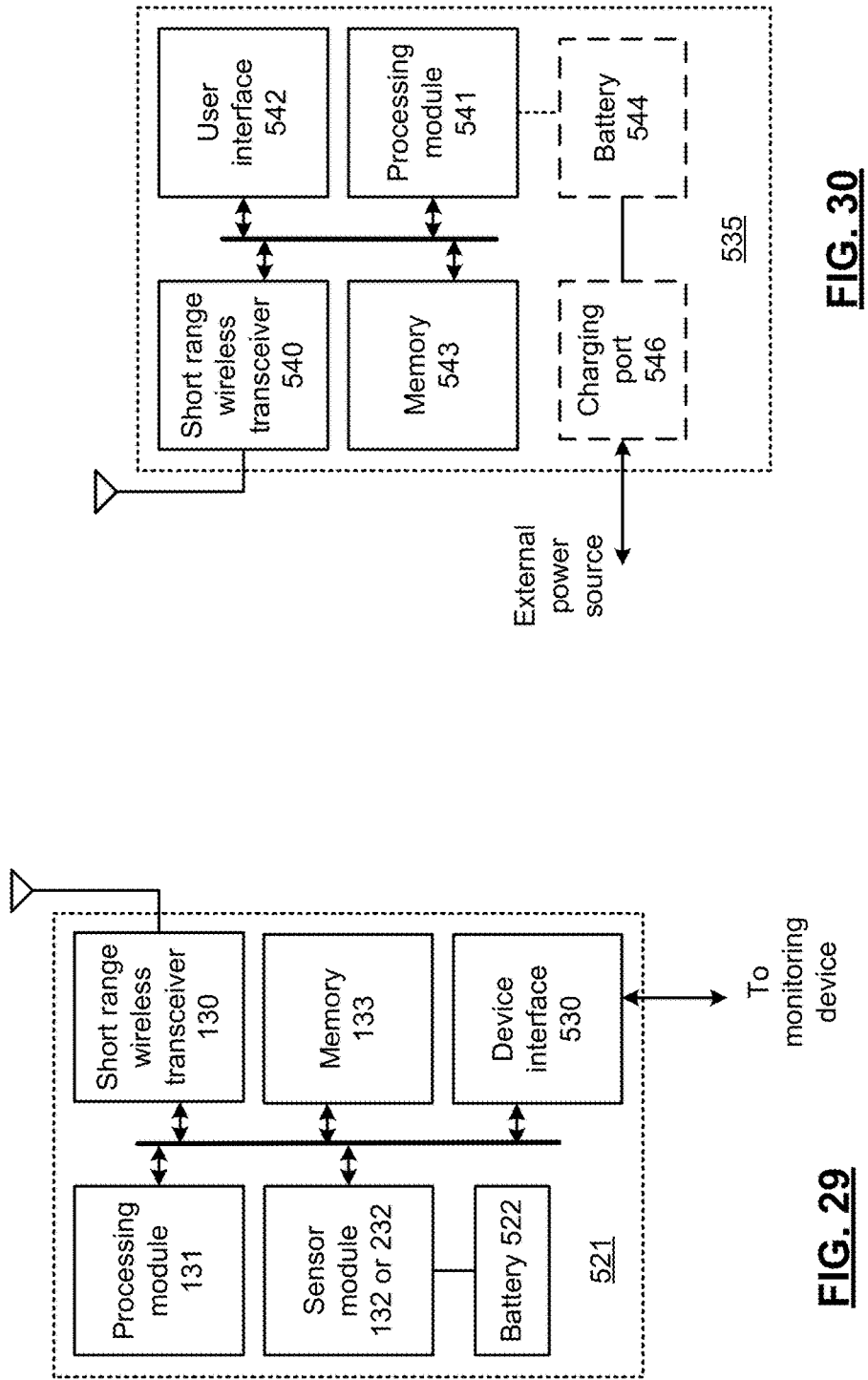

METHOD, SYSTEM AND DEVICE FOR MONITORING PROTECTIVE HEADGEAR

CROSS REFERENCE TO RELATED APPLICATIONS

The present U.S. Utility Patent Application claims priority pursuant to 35 U.S.C. § 120 as a continuation of U.S. Utility application Ser. No. 13/586,424 entitled "METHOD, SYSTEM AND DEVICE FOR MONITORING PROTECTIVE HEADGEAR", filed Aug. 15, 2012, claims priority pursuant to 35 U.S.C. § 119(e) to U.S. Provisional Application No. 61/623,189, entitled "METHOD, SYSTEM, DEVICE AND PROTECTIVE HEADGEAR", filed Apr. 12, 2012; and U.S. Provisional Application No. 61/558,764, entitled "METHOD, SYSTEM AND WIRELESS DEVICE FOR MONITORING PROTECTIVE HEADGEAR", filed Nov. 11, 2011, all of which are hereby incorporated herein by reference in their entirety and made part of the present U.S. Utility Patent Application for all purposes.

U.S. Utility application Ser. No. 13/586,424 also claims priority under 35 USC 120 as a continuation-in-part to U.S. Utility application Ser. No. 12/713,316, entitled "SYSTEM AND WIRELESS DEVICE FOR LOCATING A REMOTE OBJECT", filed on Feb. 26, 2010; the contents of which is expressly incorporated herein in its entirety by reference thereto.

BACKGROUND OF THE INVENTION

Technical Field of the Invention

The present invention relates to wireless communication devices and further to protective headgear.

Description of Related Art

As is known, wireless communication devices are commonly used to access long range communication networks as well as broadband data networks that provide text messaging, email services, Internet access and enhanced features such as streaming audio and video, television service, etc., in accordance with international wireless communications standards such as 2G, 2.5G, 3G and 4G. Examples of such networks include wireless telephone networks that operate cellular, personal communications service (PCS), general packet radio service (GPRS), global system for mobile communications (GSM), and integrated digital enhanced network (iDEN).

Many wireless telephones have operating systems that can run applications that perform additional features and functions. Apart from strictly wireless telephony and messaging, wireless telephones have become general platforms for a plethora of functions associated with, for example, navigational systems, social networking, electronic organizers, audio/video players, shopping tools, and electronic games. Users have the ability to choose a wireless telephone and associated applications that meet the particular needs of that user.

U.S. Pat. Nos. 5,539,935, 6,589,189, 6,826,509, 6,941,952, 7,570,170 and published U.S. Patent Application number 2006/0189852 describe systems that attach accelerometers to a protective helmet, either on the exterior of the helmet itself, or on the surface of the pads forcing sensors into direct contact with the wearer's head. Some use a single sensor (1, 2 or 3 axis), while others use sensors positioned at various locations on the head or helmet. An example is U.S. Pat. No. 6,826,509 that describes a specific orientation of the accelerometer's axis with respect to the skull of the wearer and describes a method that estimates the point of impact contact, the direction of force applied, and the duration of an impact in terms of its acceleration. The method of calculating these parameters applies an error-minimizing scheme that "best fits" the array of accelerometer inputs. The common goal of all such systems is to determine if an impact event has exceeded a threshold that would warrant examining the individual involved for signs of a concussion and possible removal from the activity. Some systems combine the impact threshold information with some form of follow-up physiological evaluation such as memory, eye sight, balance, or awareness tests. These tests purportedly determine if a concussion has occurred and provide some insight into its severity. Another goal of some systems is to provide information about the impact event that may be helpful in diagnosis and treatment, such as a display of the point of impact, direction, and duration of an acceleration overlaid on a picture of a head.

The disadvantages of conventional approaches will be evident to one skilled in the art when presented the disclosure that follows.

BRIEF SUMMARY OF THE INVENTION

The present invention is directed to various system, apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWINGS

FIG. 1 presents a pictorial representation of a system for monitoring protective headgear in accordance with an embodiment of the present invention.

FIG. 2 presents a pictorial representation of handheld communication device 110 and adjunct device 100 in accordance with an embodiment of the present invention.

FIG. 3 presents a pictorial representation of handheld communication device 110 and adjunct device 100 in accordance with an embodiment of the present invention.

FIG. 5 presents a pictorial representation of a system for monitoring protective headgear in accordance with an embodiment of the present invention.

FIG. 6 presents a schematic block diagram of a sensor module 132 in accordance with an embodiment of the present invention.

FIG. 7 presents a schematic block diagram of a processing module 131 in accordance with an embodiment of the present invention.

FIG. 8 presents a graphical representation of aggregate acceleration data as a function of time in accordance with an embodiment of the present invention.

FIG. 9 presents a schematic block diagram of a wireless device 121 in accordance with an embodiment of the present invention.

FIG. 10 presents a schematic block diagram of a sensor module 232 in accordance with an embodiment of the present invention.

FIG. 20 presents a flowchart representation of a method in accordance with an embodiment of the present invention.

FIG. 21 presents a flowchart representation of a method in accordance with an embodiment of the present invention.

FIG. 22 presents a flowchart representation of a method in accordance with an embodiment of the present invention.

FIG. 23 presents a flowchart representation of a method in accordance with an embodiment of the present invention.

FIG. 24 presents a flowchart representation of a method in accordance with an embodiment of the present invention.

FIG. 29 presents a schematic block diagram of a wireless device 521 in accordance with an embodiment of the present invention.

FIG. 30 presents a schematic block diagram of a wireless device 535 in accordance with an embodiment of the present invention.

DETAILED DESCRIPTION OF THE INVENTION

Figure 4:
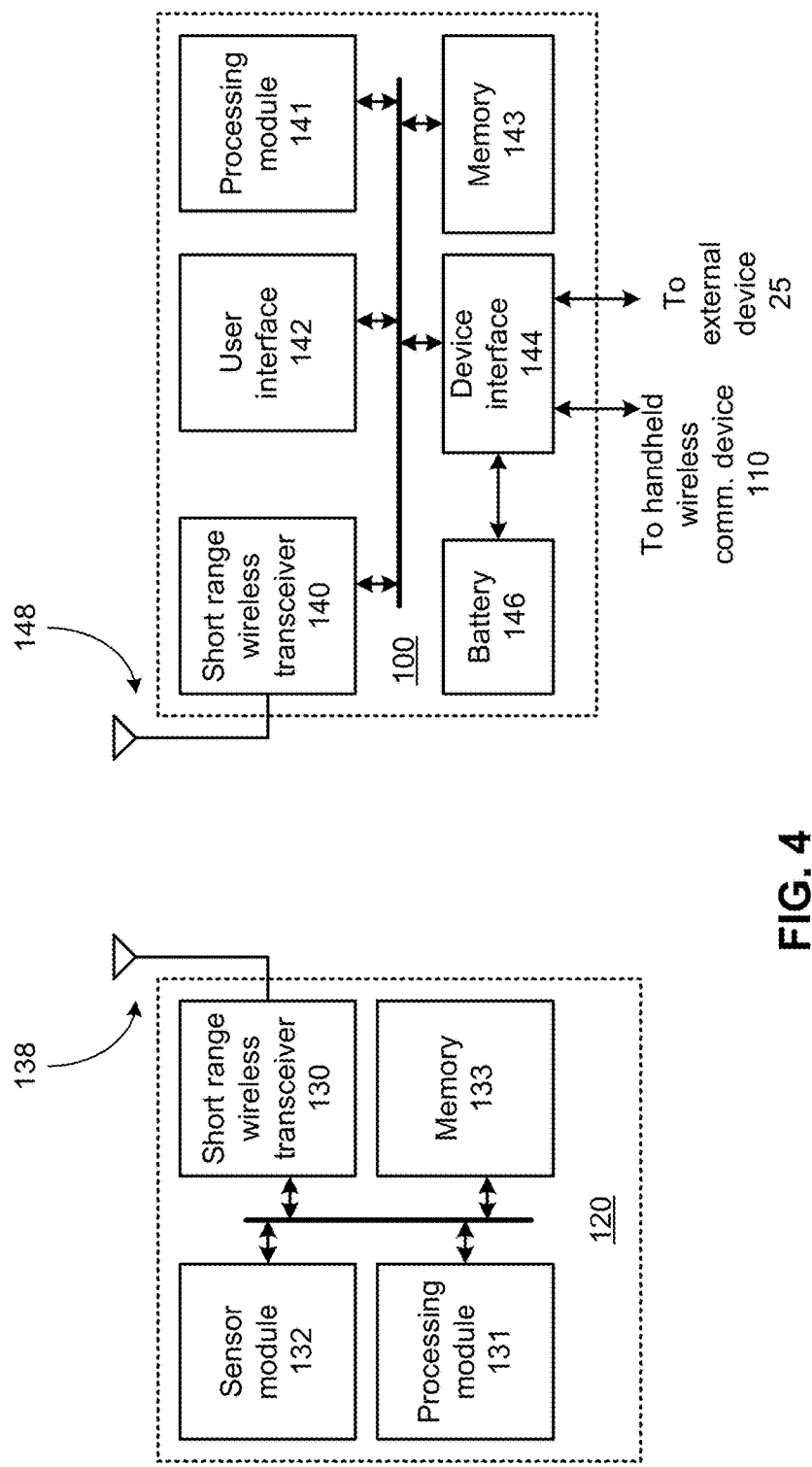
FIG. 4 presents a schematic block diagram of a wireless device 120 and adjunct device 100 in accordance with an embodiment of the present invention.

FIG. 1 presents a pictorial representation of a system for monitoring protective headgear in accordance with an embodiment of the present invention. In particular, a handheld communication device 110, such as a smart phone, digital book, netbook, personal computer with wireless data communication or other wireless communication device includes a wireless transceiver for communicating over a long range wireless network such as a cellular, PCS, CDMA, GPRS, GSM, iDEN or other wireless communications network and/or a short-range wireless network such as an IEEE 802.11 compatible network, a Wimax network, another wireless local area network connection or other communications link. Handheld communication device 110 is capable of engaging in wireless communications such as sending and receiving telephone calls and/or wireless data in conjunction with text messages such as emails, short message service (SMS) messages, pages and other data messages that may include multimedia attachments, documents, audio files, video files, images and other graphics. Handheld communication device 110 includes one or more processing devices for executing other applications and a user interface that includes, for example, buttons, a display screen such as a touch screen, a speaker, a microphone, a camera for capturing still and/or video images and/or other user interface devices.

A wireless device 120 is mounted in or otherwise coupled to a piece of protective headgear 30. The wireless device 120 includes a sensor module that generates sensor data in response to an impact to the protective headgear 30. Wireless device 120 further includes a short-range wireless transmitter that transmits a wireless signal, such as a radio frequency (RF) signal, magnetic signal, infrared (IR) signal or other wireless signal that includes data, such as event data 16 or other data that indicates, for example, data pertaining to an impact on the protective headgear. The short-range wireless transmitter can be part of a transceiver that operates in conjunction with a communication standard such as 802.11, Bluetooth, 802.15.4 standard running a ZigBee or other protocol stack, ultra-wideband, an RF identification (RFID), IR Data Association (IrDA), Wimax or other standard short or medium range communication protocol, or other protocol.

While protective headgear 30 is styled as a football helmet, the present invention can be implemented in conjunction with other protective headgear including a hat, headband, mouth guard or other headgear used in sports, a hard hat or other industrial protection gear, other headgear and helmets worn by public safety or military personnel or other headgear or helmets. In addition, protective headgear can include a face mask, face guard, skull cap, chin strap, an ear piece such as ear plugs, a hearing aide, an ear mounted transceiver, an ear piece in contact with the bony area of the skull behind the ear or other ear piece or other gear that is either a separate component or is integrated with other headgear or other gear. In particular, protective headgear includes, but is not limited to, gear that is used to reduce vibration, dissipate impact energy from an impact event, control the rate of energy dissipation in response to an impact event and/or to provide real-time or non-real-time monitoring and analysis of impact events to the region of the head and neck of a wearer of the protective gear.

Adjunct device 100 includes a housing that is coupleable to the handheld communication device 110 via a communication port of the handheld communication device 110. The adjunct device 100 includes a short-range wireless receiver that receives a wireless signal from the wireless device 120 that includes data, such as event data 16. The short-range wireless receiver of adjunct 100 can also be part of a transceiver that operates in conjunction with a communication standard such as 802.11, Bluetooth, 802.15.4 standard running a ZigBee or other protocol stack, ultra-wideband, Wimax or other standard short or medium range communication protocol, or other protocol. In particular, the short-range wireless receiver of adjunct device 100 is configured to receive the event data 16 or other data generated by wireless device 120.

Adjunct device includes its own user interface having push buttons 20, sound emitter 22 and light emitter 24 that optionally can emit audio and/or visual alert signals in response to the event data 16. As with the user interface of wireless device 120, the user interface of adjunct device 100 can similarly include other devices such as a touch screen or other display screen, a thumb wheel, trackball, and/or other input or output devices. While shown as a plug-in module, the adjunct device 100 can be implemented as either a wireless gateway or bridge device or a case or other housing that encloses or partially encloses the handheld communication device 100.

In operation, event data 16 is generated by wireless device 120 in response to an impact to the protective headgear 30. The event data 16 is transmitted to the adjunct device 100 that transfers the event data 16 to the handheld communication device 110 either wirelessly or via the communication port of the handheld communication device 110. The handheld communication device 110 executes an application to further process the event data 16 to, for example, display a simulation of the head and/or brain of the wearer of the protective headgear 30 as a result of the impact.

The further operation of wireless device 120, adjunct device 100 and handheld communication device 100, including several optional implementations, different features and functions spanning complementary embodiments are presented in conjunction with FIGS. 2-43 that follow.

FIGS. 2 and 3 present pictorial representations of handheld communication device 110 and adjunct device 100 in accordance with an embodiment of the present invention. As shown in FIG. 2, adjunct device 100 and handheld communication device 110 are decoupled. Handheld communication device 110 includes a communication port 26' and adjunct device 100 includes a mating plug 26 for coupling the adjunct device 100 to the communication port 26' of handheld communication device 110. In an embodiment of the present invention, the communication port 26' and plug 26 are configured in conjunction with a standard interface such as universal serial bus (USB), Firewire, or other standard interface, however, a device specific communication port such as an Apple iPod/iPhone port, a Motorola communication port or other communication port can likewise be employed. Further, while a physical connection is shown, a wireless connection, such as a Bluetooth link, 802.11 compatible link, an RFID connection, IrDA connection or other wireless connection can be employed in accordance with alternative embodiments.

As shown in FIG. 3, adjunct device 100 is coupled to the handheld communication device 110 by plug 26 being inserted in communication port 26'. Further, adjunct device 100 includes its own communication port 28' for coupling, via a mating plug 28, the adjunct device 100 to an external device 25, such as a computer or other host device, external charging device or peripheral device. In an embodiment of the present invention, the communication port 28' and plug 28 are configured in conjunction with a standard interface such as universal serial bus (USB), Firewire, or other standard interface, however, a device specific communication port such as an Apple iPod/iPhone port, a Motorola communication port or other communication port can likewise be employed.

In an embodiment of the present invention, the adjunct device passes signaling between the external device 25 and the handheld communication device 110 including, for instance, charging signals from the external connection and data communicated between the handheld communication device 110 and the external device 25. In this fashion, the external device can communicate with and/or charge the handheld communication device with the adjunct device 100 attached, via pass through of signals from plug 28 to communication port 26'. It should be noted however, that while communication ports 28' and 26' can share a common physical configuration, in another embodiment of the present invention, the communication ports 28' and 26' can be implemented via different physical configurations. For example, communication port 26' can be implemented via a device specific port that carries USB formatted data and charging signals and communication port 28' can be implemented via a standard USB port. Other examples are likewise possible.

In an embodiment of the present invention, when the adjunct device 100 is coupled to handheld communication device 110, the adjunct device 100 initiates communication via the communication port 26' to determine if an application is loaded in the handheld communication device 110—to support the interaction with the adjunct device 100. Examples of such applications include a headgear monitoring application or other application that operates in conjunction with the adjunct 100. If no such application is detected, the adjunct 100 can communicate via communication port 26' to initiate a download of such an application directly or to send the browser of the handheld communication device 110 to a website store at a remote server or other location where supporting applications can be browsed, purchased or otherwise selected for download to the handheld communication device 110.

In a further embodiment of the present invention, when a supporting application is loaded in handheld communication device 110, the handheld communication device 110 initiates communications via the communication port 26' to determine if an adjunct device 100 is coupled thereto or whether or not an adjunct device has never been coupled thereto. If no such adjunct device 100 is detected, the application can instruct the user to connect the adjunct device 100. Further, the application can, in response to user selection and/or an indication that an adjunct device has not been previously coupled to the handheld communication device 110, automatically direct a browser of the handheld communication device 110 to a website store at a remote server or other location where a supporting adjunct devices 100 can be selected and purchased, in order to facilitate the purchase of an adjunct device, via the handheld communication device 110.

In a further embodiment, the application maintains a flag that indicates if an adjunct device 100 has previously been connected. In response to an indication that an adjunct device has not been previously coupled to the handheld communication device 110, the application can automatically direct a browser of the handheld communication device 110 to a website store at a remote server or other location where a supporting adjunct devices 100 can be selected and purchased, in order to facilitate the purchase of an adjunct device, via the handheld communication device 110.

FIG. 4 presents a schematic block diagram of a wireless device 120 and adjunct device 100 in accordance with an embodiment of the present invention. In particular, wireless device 120 includes short-range wireless transceiver 130 coupled to antenna 138, processing module 131, sensor module 132 and memory 133. While not expressly shown, wireless device 120 can include a replaceable battery for powering the components of wireless device 120. In the alternative, wireless device 120 can include a battery that is rechargeable via an external charging port, for powering the components of wireless device 120. In addition, the wireless device 120 can be powered in whole or in part via any electromagnetic or kinetic energy harvesting system, such as an electromagnetic carrier signal in a similar fashion to a passive RF tag or passive RFID device, via a piezoelectric element that generates a voltage and current in response to motion or in response to an impact event, or via a mass spring system having a magnet that moves through a coil to generate current in response to device motion and/or via capacitive storage of a charge sufficient to power the wireless device 120 for short intervals of time, such as during an event window. Adjunct device 100 includes short-range wireless transceiver 140 coupled to antenna 148, processing module 141, user interface 142 and memory 143, device interface 144, and battery 146. The processing modules 131 and 141 control the operation of the wireless device 120 and adjunct device 100, respectively and provide further functionality described in conjunction with, and as a supplement to, the functions provided by the other components of wireless device 120 and adjunct device 100.

As discussed in conjunction with FIGS. 1-4, the short-range wireless transceivers 130 and 140 each can be implemented via a transceiver that operates in conjunction with a communication standard such as 802.11, Bluetooth, 802.15.4 standard running a ZigBee or other protocol stack, ultra-wideband, RFID, IrDA, Wimax or other standard short or medium range communication protocol, or other protocol. User interface 142 can contain one or more push buttons, a sound emitter, light emitter, a touch screen or other display screen, a thumb wheel, trackball, and/or other user interface devices.

The processing module 131 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 133. Note that when the processing module 131 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 133 stores, and the processing module 131 executes, operational instructions corresponding to at least some of the steps and/or functions illustrated herein.

The memory module 133 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of wireless device 120 are shown as being coupled by a particular bus structure, other architectures are likewise possible that include additional data busses and/or direct connectivity between components. Wireless device 120 can include additional components that are not expressly shown.

Likewise, the processing module 141 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 143. Note that when the processing module 141 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 143 stores, and the processing module 141 executes, operational instructions corresponding to at least some of the steps and/or functions illustrated herein.

The memory module 143 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of adjunct device 100 are shown as being coupled by a particular bus structure, other architectures are likewise possible that include additional data busses and/or direct connectivity between components. Adjunct device 100 can include additional components that are not expressly shown.

As shown, the adjunct device includes a battery 146 that is separate from the battery of the handheld communication device 110 and can supply power to short-range wireless transceiver 140, processing module 141, user interface 142, memory 143, and device interface 144 in conjunction with a power management circuit, one or more voltage regulators or other supply circuitry. By being separately powered from the handheld communication device 110, the adjunct 100 can operate even if the battery of the handheld communication device is discharged.

Device interface 144 provides an interface between the adjunct device 100 and the handheld communication device 110 and an external device 25, such as a computer or other host device, peripheral or charging unit. As previously discussed in conjunction with FIGS. 1-4, the housing of adjunct device 100 includes a plug, such as plug 26, or other coupling device for connection to the communication port 26' of the handheld communication device 110. In addition, the housing of adjunct device 100 further includes its own communication port, such as communication port 28 or other coupler for connecting to an external device 25. Device interface 144 is coupled to the communication port 28 that operates as a charging port. When adjunct device 100 is connected to an external source of power, such as external device 25, device interface 144 couples a power signal from the external power source to charge the battery 146. In addition, the device interface 144 couples the power signal from the external power source to the communication port of the handheld communication device 110 to charge the battery of the handheld communication device. In this fashion, both the handheld communication device 110 and the adjunct device 100 can be charged at the same time or staged in a priority sequence via logic contained in the adjunct device 110 that, for example, charges the handheld communication device 110 before the adjunct device 100 or vice versa. Further, the handheld communication device 110 can be charged while the devices are still coupled—without removing the adjunct device 100 from the handheld communication device 110.

While the battery 146 is separate from the battery of the handheld communication device 110, in an embodiment of the present invention, the device interface 144 is switchable between an auxiliary power mode and a battery isolation mode. In the battery isolation mode, the device interface 144 decouples the battery 146 from the battery of the handheld communication device 110, for instance, to preserve the charge of battery 146 for operation even if the battery of the handheld communication device 110 is completely or substantially discharged. In the auxiliary power mode, the device interface 144 couples the power from the battery 146 to the handheld communication device 110 via the communication port to either charge the battery of the handheld communication device 110 via power from the battery 146 or to charge the battery 146 from the battery of handheld device 110. In this fashion, the user of the handheld communication device 110 at or near a discharged state of the handheld communication device battery could opt to draw power from the battery 146. In an embodiment of the present invention, signaling from user interface 142 could be used to switch the device interface 144 between the battery isolation mode and the auxiliary power mode. Alternatively or in addition, signaling received from the handheld communication device via the communication port, or remotely from wireless device 120, could be used to switch the device interface 144 between the battery isolation mode and the auxiliary power mode.

Device interface 144 includes one or more switches, transistors, relays, or other circuitry for selectively directing the flow of power between the external device 25, the battery 146, and the handheld communication device 110 as previously described. In addition, the device interface 144 includes one or more signal paths, buffers or other circuitry to couple communications between the communication port of the adjunct device 110 and the communication port of the handheld communication device 110 to pass through communications between the handheld communication device 110 and an external device 25. In addition, the device interface 144 can send and receive data from the handheld communication device 110 for communication between the adjunct device 100 and handheld communication device 110.

FIG. 5 presents a pictorial representation of a system for monitoring protective headgear in accordance with an embodiment of the present invention. In particular, an embodiment is presented that includes elements that have been previously described in conjunction with FIG. 1 and are referred to by common reference numerals. In this embodiment however, protective headgear 30 includes a plurality of wireless devices 120 that are designated as (120, 120' . . . ). Each of the wireless devices (120, 120' . . . ) is capable of operating independently and generating event data (16, 16' . . . ) in response to the motion the corresponding sensor modules of the respective wireless devices (120, 120' . . . ).

In operation, event data (16, 16' . . . ) is generated by wireless devices (120 and/or 120' . . . ) in response to an impact to the protective headgear 30. The event data (16, 16' . . . ) is transmitted to the adjunct device 100 that transfers the event data (16, 16' . . . ) to the handheld communication device 110 via the communication port of the handheld communication device 110. The communication device executes an application to further process the event data (16, 16' . . . ) to display a simulation of the head of the wearer of the protective headgear 30 as a result of the impact. The presence of multiple wireless devices (120, 120' . . . ) with a corresponding plurality of separate sensor modules 132 allow more comprehensive modeling of the impact by the protective headgear monitoring application.

FIG. 6 presents a schematic block diagram of a sensor module 132 in accordance with an embodiment of the present invention. As shown, sensor module 132 includes an accelerometer 200, a gyroscope 202 and a device interface 204 and generates sensor data 206 that includes both linear acceleration data and rotational acceleration data. The accelerometer 200 can include a piezoresistive accelerometer, piezoelectric accelerometer, capacitive accelerometer, a quantum tunneling accelerometer, a micro electro-mechanical system (MEMS) accelerometer or other accelerometer. In operation, accelerometer 200 is coupled to the protective headgear 30 and responds to acceleration of the protective headgear along a plurality of translational axes and generates linear acceleration data that indicates the acceleration of the protective headgear along 1, 2 or 3 axes such as an x axis, y axis and z axis. Similarly, gyroscope 202 responds to acceleration of the protective headgear along a plurality of axes such as a roll axis, pitch axis and yaw axis and wherein the rotational acceleration data indicates the acceleration of the protective headgear along the plurality of axes. Gyroscope 202 can be implemented via a vibrating element gyroscope, a MEMS gyroscope or other gyroscopic sensor.

The device interface 204 includes device drivers for selectively driving the accelerometer 200 and/or gyroscope 202 and an analog to digital convertor for generating sensor data 206 in response to analog signaling generated by the accelerometer 200 and gyroscope 202. While shown as a separate device, the functionality of device interface 204 can be included in the accelerometer 200 and/or the gyroscope 202.

The use of both an accelerometer and a gyroscope in each sensor module (referred to as a pad) removes the need for a large number of pads. This is partly accomplished by providing both linear and angular acceleration output, and can further be aided by constraining the interpretation of sensor outputs to be consistent with a physical model of the system—which may include the helmet, neck bones and musculature, skull, cerebral fluid, and brain. While only one sensor pad is required when coupled with the physical model of the head, adding multiple sensor pads allows us to account for some types of measurement and modeling errors.

FIG. 7 presents a schematic block diagram of a processing module 131 in accordance with an embodiment of the present invention. As shown, device processing module 131 includes an event detection module 220 and an event processing module 222. The event detection module 220 and event processing module 222 can each be implemented as independent or shared hardware, firmware or software, depending on the implementation of processing module 131. The event detection module 220 analyzes the sensor data 206 and triggers the generation of the event data in response to detection of an event in the sensor data 206.

While some prior art systems judge impact merely based on acceleration, acceleration alone does not tell the whole story. For example, quickly striking a sensor pad with a ballpoint pen can generate acceleration values in the 200 to 300 G range excess of 100 G's for a short time, but this type of impact would hardly be considered dangerous. This type of analysis does not fully account for mass or momentum. Impact measurement is more about energy dissipation rates, or power and/or peak power, potential applied in an oscillating fashion, that is delivered to the head during an impact event. In an embodiment of the present invention, the event processing module 222 analyzes the sensor data 206 to generate event data 16 that include power data that is calculated based on a function of velocity data and acceleration data as a function of time.

For example, consider the example where the sensor module 132 includes a three-axis accelerometer and a three axis gyroscope and wherein sensor data 206 is represented by an acceleration vector A(t), where:

$$A(t)=(\ddot{x}_1,\ddot{x}_2,\ddot{x}_3)$$

And where, $\ddot{x}_i$ is the linear acceleration along the ith axis.

It should be noted that acceleration, A (t), referred above, is raw acceleration from all sources (including gravitational acceleration) and not simply acceleration due to an impact event, exclusive of gravitational acceleration. The quantity a(t,) a calibrated event acceleration, which removes the acceleration of gravity, may be defined as follows:

$$a(t)=A(t)C-G(t)$$

Where: G(t) expresses the pull of gravity on the accelerometer, and C is a matrix containing static linear calibration values for each axis of the accelerometer. It should also be understood that the linear calibration matrix C could be replaced by a non-linear function or by a table of values expressing a linear, non-linear function, or non-static calibration.

As shown above, the direction of gravity can be used to more accurately calculate all acceleration dependent values. The starting direction of gravity, $G(t_o)$ at time $t_o$, from the 3-axis accelerometer during a quiescent period, can be used to calculate the direction of gravity throughout an impact event using the 3-axis gyroscope as follows:

$$\phi(t)=\int w(t)dt$$

Where $\phi(t)$ represents the change in orientation over the integral (in polar coordinates). The angular acceleration $a_a(t)$, can be determined based on $$a_a(t)=\partial/\partial t[w(t)]$$

where w(t) is calibrated angular velocity from the gyroscope 202. The direction of gravity G(t) can be found based on:

$$G(t)=G(t_o)+rect[\phi(t)]$$

High-g accelerometers may not be sensitive enough to accurately determine the direction of gravity, so a low-g sensor can be employed. On the other hand, expected impact events may exceed the range of a low-g sensor, necessitating a high-g sensor. In an embodiment of the invention, accelerometer 200 includes both a low-g accelerometer, a high-g accelerometer. The low-g accelerometer portion of accelerometer 200 can be employed to determine the direction of gravity as follows. Sensor data is organized into windows with defined start and end times. Sample windows start when the accelerometer 200 and gyroscope 202 are simultaneously quiescent. The sample windows continue when one or more threshold events occur, and end when the gyroscope 202 and accelerometer 200 are simultaneously quiescent a second time. Note the end of one sample window may act as the start of another.

In this embodiment, the low-g portion of accelerometer 200 accurately indicates its orientation with respect to gravity only during quiescent or near quiescent periods, which by definition occur at the start and end of a sample window. If we take $G(t_o)$ to be the average orientation of the low-g sensor at the window start, this term in combination with the calibrated gyro output w(t), can be used to calculate the orientation of gravity throughout the sample window. In a similar fashion, the calculated orientation of gravity at the end of the window, can be compared to the measured value with the difference being used for error detection and correction.

A number of tests for quiescence may be employed. A simple test is when a predetermined number of consecutive samples of the low-g portion of accelerometer 200 have an average norm, n(t), that is approximately equal to 1 g where $$n(t)=|a(t)|$$

For example, a quiescent state is indicated where a consecutive number of samples satisfy the condition:

$$1-e<n(t)<1+e$$

where e represents a tolerance.

Other more robust tests may be employed, for example, where all sensors and all axes must be simultaneously quiescent, as dynamically determined according to some test of statistical significance, whose individual estimated statistics meet one or more criteria, such as the norm of the estimated statistics of the low-g sensor not exceeding 1+e.

In another embodiment of the present invention, the event detection module 220 analyzes the sensor data by generating aggregate acceleration data from the sensor data 206 and comparing the aggregate acceleration data to an acceleration threshold. Event detection module 220 determines an event window that indicates an event time period that spans the event $t_o \leq t \leq t_f$ based on comparing the aggregate acceleration data to an acceleration threshold. The event detection module 220 triggers the generation of the event data 16 by the event processing module 222, based on this event window. In particular, the event detection module 220 triggers the event processing module 222 to begin generating the event data 16 after the event window ends. The event processing module 222 generates the event data 16 by analyzing the sensor data 206 corresponding to the event window determined by the event detection module 220.

Considering again the example where the sensor module 132 includes a three-axis accelerometer and a three axis gyroscope and wherein sensor data 206 includes a vector B of translational acceleration and angular velocity, where:

$$B=(\ddot{x}_1,\ddot{x}_2,\ddot{x}_3,\dot{\theta}_1,\dot{\theta}_2,\dot{\theta}_3)$$

The event detection module 220 generates an aggregate acceleration and aggregate angular velocity as, for example, the norm of the vector B, and determines the event window $t_1 \leq t \leq t_2$, as the time period where $|B| \geq T_a$, where $T_a$ represents an aggregate threshold. It should be noted that while a single aggregate threshold 212 is described above, two different thresholds could be employed to implement hysteresis in the generation of the event window. Further while the vector norm is used as a measure of aggregate acceleration and angular velocity, a vector magnitude, or other vector or scalar metrics could be similarly employed. In addition, while event processing module 222 is described as being implemented in the processing module 131 of the wireless device 120, in a further embodiment of the present invention, the event detection module 220 can trigger the generation of event data 16 that merely includes the sensor data 206 during the time window and the functionality of event processing module 222 can be implemented in conjunction with a processing device of the handheld communication device 110 in conjunction with the protective headgear monitoring application.

A portion of the total energy generated at impact is not easily calculated from accelerometer data—that portion which produces no bulk motion, and instead is dissipated within the helmet's structure or mechanically transferred to objects or surfaces in contact with the helmet. So long as no structural limit of the helmet is exceeded, such impact energy can be ignored. Consider the example where a helmet is in contact with the ground and the impact produces no motion of the helmet.

That portion of impact energy producing motion, perhaps violent motion of the helmet, is of great interest from a personal injury standpoint. Energy of motion, or kinetic energy, is calculable from accelerometer data. The rate at which kinetic energy is imparted and then dissipated, or power, is a consistent indicator of the potential for brain injury from an impact event.

In an embodiment of the present invention, power data can be determined based on a calculation of the mechanical power corresponding to an impact event. The mechanical power P(t) represents a rate of force applied through a distance and over an event window $t_1 \leq t \leq t_2$, and where force is calculated as the product of mass, m, and acceleration as follows:

$$P(t) = m\frac{\partial}{\partial t}\left[a(t)\int_{t_1}^{t_2}\int a(t)dt dt\right]$$
$$= m[a(t)v(t)]$$

Mass in this case is the estimated mass of the entire system including the head and the protective headgear, and where the velocity v(t) can be found based on:

$$v(t) = \int a(t)dt$$
$$= (\dot{x}_1, \dot{x}_2, \dot{x}_3)$$

This form of event data 16 more closely represents power of impact to the protective headgear.

In other embodiments, power data, different from mechanical power can be employed in favor of other power-related data that is not strictly dependent on the mass of the head helmet system. As previously discussed, the mechanical power can be expressed as:

$$P(t)=m[+a(t)v(t)]$$

The mass m can be expressed in terms of the volume u and average density d of the head and helmet system as:

$$m=du$$

Power data can be based on a power diffusion q(t) expressed as follows:

$$q(t) = \frac{P(t)}{u} = d[a(t)v(t)]$$

Considering that the average density of the head helmet system is a constant, the power diffusion q(t) is proportional to a related power diffusion term Q(t) that is calculated as:

$$Q(t) = \frac{P(t)}{m} = [a(t)v(t)]$$

Expressing the kinetics of an impact based on either of the power diffusion terms q(t) or Q(t) allows the power data to be computed without accounting for the mass of the entire system, providing a normalized metric useful in assessing the severity of an impact event. While power has been described above in linear-translational terms, it is possible to develop power metrics in rotational-torsional terms. Any of the power terms P(t), q(t), Q(t), previously described in terms of only linear (translational) motion can be calculated instead in terms of rotational motion or a combination of linear and rotational motion. For example, rotational kinetics, such as the quantity β(t) presented below, can be a factor in assessing the potential for brain injury and can, in particular, be considered either alone or in combination with translational kinetics.

$$\beta(t)=a_a(t)w(t)$$

It follows that the event data 16 can include a(t), v(t), x(t), q(t), Q(t), $a_a(t)$, w(t), φ(t), β(t), along with similar quantities, any intermediate calculations or raw data used to calculate any of these quantities. In particular a(t), v(t), x(t), q(t), Q(t), $a_a(t)$, w(t), φ(t), β(t) and other measured or calculated quantities can be employed in a number of useful ways. In addition, event data 16 can include data that is already processed in the form of simulation data or other display data. Such as applying individual or compound thresholds to determine if an injury event may have occurred, or in preparing useful simulations and displays, involving animations and/or color maps to express impact severity or to provide educational displays to increase awareness among coaches, players, medical personnel and parents in a sports setting, and to others in the context of law enforcement, industrial applications, and other uses of protective headgear 30. In particular event data 16 can also include a system status such as a battery status, low battery indicator, system ready indicator, system not ready indicator or other status. Event data 16 can also include force data derived from a strain gauge load cell or other sensor, energy data or other power data and power diffusion data.

It should also be noted that event data 16 can include merely an alarm indication in a failsafe mode of operation. For example in circumstances where an event window begins, however due to low power, a fault condition or other error, particular values of a(t), v(t), x(t), q(t), Q(t), $a_a$(t), w(t), φ(t) cannot be calculated or are deemed to be unreliably calculated due to an internal error detection routine, the event data 16 can merely include an alarm signal that is sent to adjunct device 100 to trigger an alarm in the handheld communication device 110 of a potential high impact event that cannot be analyzed. Further, event data 16 can include periodic status transmissions or other transmission to the adjunct device 100 indicating that the wireless device 120 is operating normally. In the absence of receiving one or more such periodic transmissions, the adjunct device 100 can trigger an alarm indicating that a wireless device has failed to check in and may be out of range, out of battery power or otherwise in a non-operational state.

FIG. 8 presents a graphical representation of aggregate acceleration data as a function of time in accordance with an embodiment of the present invention. In particular, the line 210 represents an example of aggregate acceleration data as a function of time. When the line 210 first exceeds the acceleration threshold 212 at time $t_1$, the event detection module 220 detects the beginning of an event. The event window 214 is determined based on when the aggregate acceleration next falls below the acceleration threshold 212 at time $t_2$.

As discussed in conjunction with FIG. 7, an event window is determined, for example, based on the time period between two quiescent periods. The event detection module 220 triggers the generation of the event data 16 by the event processing module 222, based on this event window. For example, the event detection module 220 triggers the event processing module 222 to begin generating the event data 16 during the event window and triggers transmitting the event data 16 either during the event window or after the event window ends. The event processing module 222 generates the event data 16 by analyzing the sensor data 206 corresponding to the event window determined by the event detection module 220.

FIG. 9 presents a schematic block diagram of a wireless device 121 in accordance with an embodiment of the present invention and FIG. 10 presents a schematic block diagram of a sensor module 232 in accordance with an embodiment of the present invention. Wireless device 121 includes many common elements of wireless device 120 that are referred to by common reference numerals and can be used in place of wireless device 120 in any of the embodiments described therewith. Wireless device 121 includes a sensor module 232 that includes a device interface 205 that operates in a similar fashion to device interface 204, yet further generates a wake-up signal 234. Wireless device 121 includes a power management module 134 that selectively powers the short-range transmitter/transceiver 130, the processing module 131 and optionally memory 133 in response to the wake-up signal. This saves power and extends battery life of wireless device 121.

In an embodiment of the present invention, the sensor module 232 generates the wake-up signal 234 when an acceleration signal from the accelerometer 200 and/or the angular velocity from the gyroscope 202 compares favorably to a signal threshold. Considering again the example where the sensor module 132 includes a three-axis accelerometer and a three axis gyroscope and wherein sensor data 206 is represented by an aggregate acceleration angular velocity vector B, where:

$$B=(\ddot{x}_1,\ddot{x}_2,\ddot{x}_3,\dot{\theta}_1,\dot{\theta}_2,\dot{\theta}_3)$$

The device interface 205 includes hardware, software or firmware that generates an aggregate acceleration as, for example, the norm of the vector B, and generates wake-up signal 234 in response to event where |B| first exceeds $T_s$, where $T_s$ represents a signal threshold. In an embodiment the signal threshold $T_s=T_a$, however other values can be employed. For example, a value of $T_s=T_a-k$, can be employed to provide a more sensitive value of the wake-up signal and further to trigger wake-up of the components of the wireless device 121 prior to the beginning of the event window. It should also be noted that a wake-up signal 234 can be generated based on the end of a quiescent period as described in conjunction with FIG. 7.

In an embodiment of the present invention, the device interface 205 directly monitors the outputs of the accelerometer 200 and/or gyroscope 202. In this case, device interface 205 generates the sensor data 206 only in response to the wake-up signal 234. In this fashion, the sensor data 206 is only generated, when needed. In another embodiment, device interface generates sensor data 206 continuously and generates wake-up signal 234 based on an analysis of the sensor data 206. While the device interface 205 has been described in the example above as using an aggregate of all the acceleration components to generate a wake-up signal, in a further embodiment, the device interface 205 may only monitor a limited subset of all axes of linear and rotational acceleration in order to wake-up the device. In this fashion, only some limited sensor functionality need be powered continuously—saving additional power.

While described above in terms of the use of accelerometer 200 or gyroscope 202 as the ultimate source of sensor data for the wake up signal, in another embodiment of the present invention, the wake-up signal is generated by a separate wake-up sensor, such as a kinetic sensor, piezoelectric device or other device that generates a wake-up signal in response to the beginning of an impact event.

Figure 11:
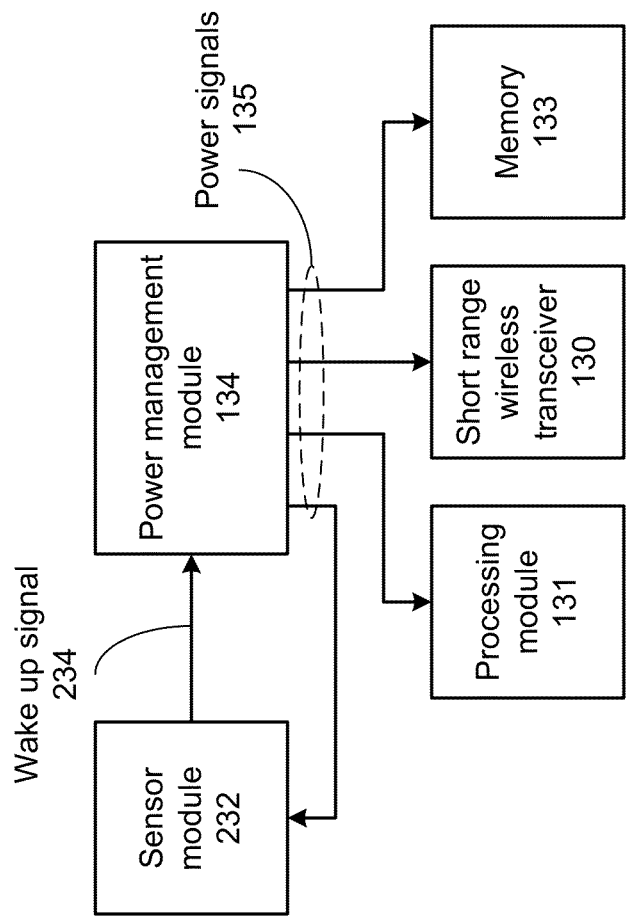
FIG. 11 presents a schematic block diagram of a power management module 134 in accordance with an embodiment of the present invention.

FIG. 11 presents a schematic block diagram of a power management module 134 in accordance with an embodiment of the present invention. As described in conjunction with FIGS. 9-10, power management module 134 selectively powers the short-range transmitter/transceiver 130, the processing module 131 and optionally memory 133 in response to the wake-up signal. Power management module generates a plurality of power signals 135 for powering these devices when triggered by the wake-up signal 234.

As shown, the power management module 134 further generates an additional power signal 135 for powering the sensor module 232 and optionally increased the power generated in response to the wake-up signal 234. In the example where device interface 205 operates with limited functionality prior to generation of the wake-up signal 234, the power is increased to sensor module 232 in order to power the devices necessary to drive the full range of sensors and further to generate sensor data 206. This can include selectively powering an analog to digital converted included in device interface 205, only in response to the wake-up signal 234.

Figure 12:
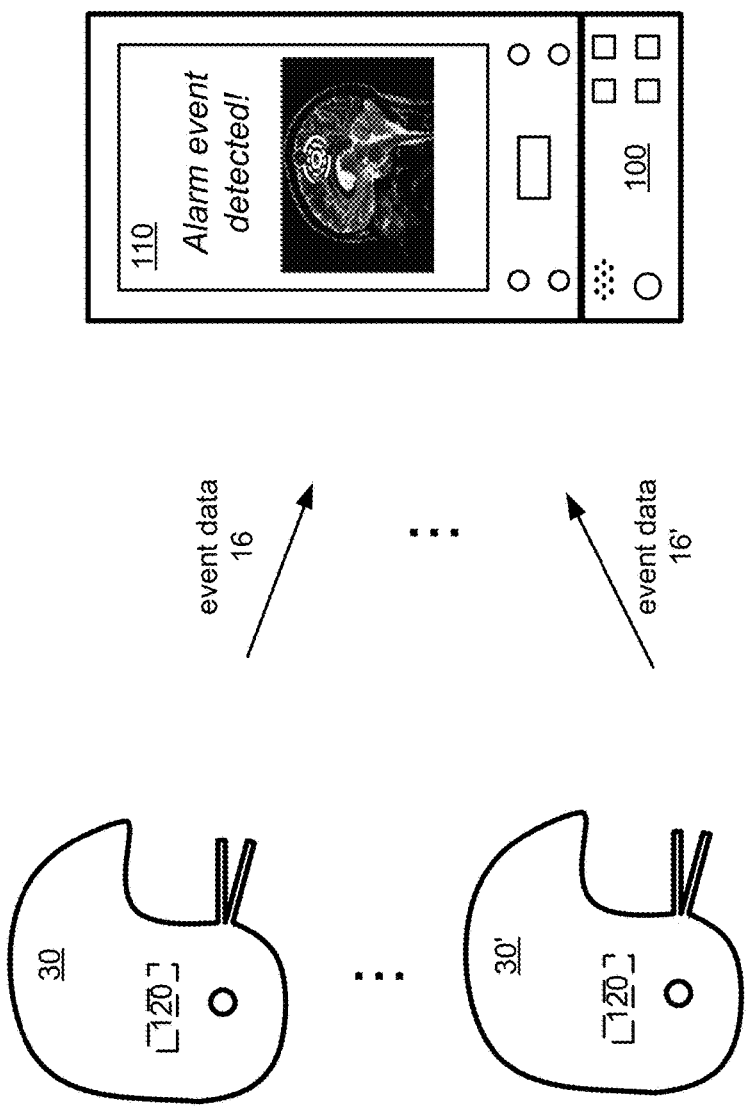
FIG. 12 presents a pictorial representation of a system for monitoring protective headgear in accordance with an embodiment of the present invention.

FIG. 12 presents a pictorial representation of a system for monitoring protective headgear in accordance with an embodiment of the present invention. In particular, a system is shown that operates in conjunction with any of the embodiments presented in conjunction with FIGS. 1-11. In this embodiment however, the adjunct device 100 and handheld communication device 110 operate to monitor a plurality of protective headgear 30. Event data (16, 16'...) from any of the plurality of protective headgear (30, 30'...) are received and used by a protective headgear monitoring application of handheld communication device 110. In operation, the application processes the event data (16, 16'...) to, for example, display a simulation of the head and/or brain of the wearer of the protective headgear 30 and/or 30' as a result of an impact.

Figure 13:
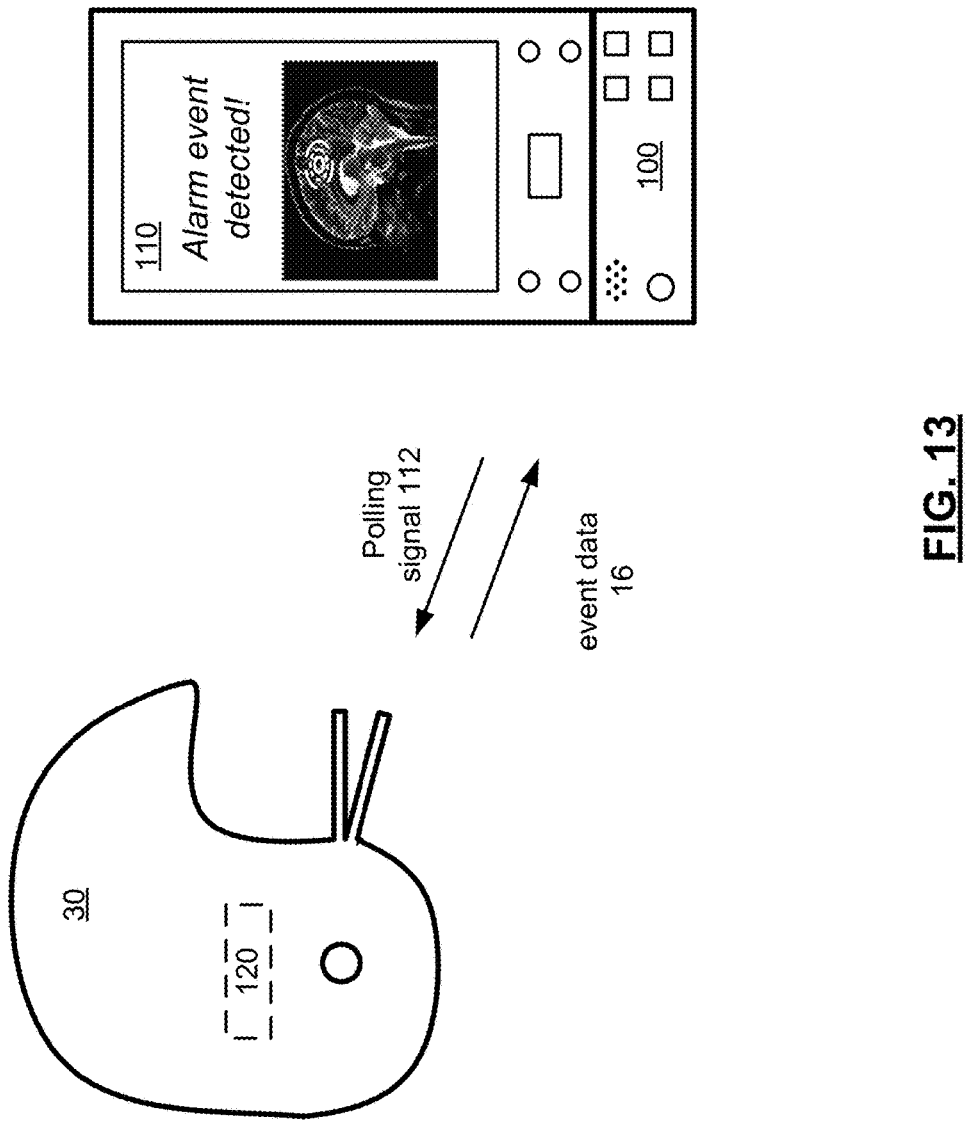
FIG. 13 presents a pictorial representation of a system for monitoring protective headgear in accordance with an embodiment of the present invention.

FIG. 13 presents a pictorial representation of a system for monitoring protective headgear in accordance with an embodiment of the present invention. As previously described, the wireless device 120 can automatically generate event data 16 in response to the detection by the wireless device 120 of an event. In this fashion, event data 16 can be pushed to an adjunct device 100. In this embodiment however, the wireless device 120 receives a polling signal 112 transmitted by adjunct device 110. In response to the polling signal 112, the wireless device 120 generates a wireless signal that contains either event data 16, a system status such as a battery status, system ready indicator, other status or other data.

For example, a parent watching a football game in the stands notices a blow to the helmet of their child. The parent launches a protective headgear monitoring application of the handheld communication device 110 that causes adjunct device 100 to emit the polling signal 112. The wireless device 120 responds to polling signal 112 by generating a wireless signal that is transmitted back to adjunct device 100. The polling signal can include event data 16. In this fashion, the event data 16 can be generated and or transmitted by wireless device 120 on demand from the user of the handheld communication device 110.

As mentioned above, other types of data can be transmitted by wireless device 120 in response to the polling signal 112. In another example, the wireless device 120 can monitor its remaining battery life and transmit battery life data to the adjunct device 100 in response to the polling signal 112. In this fashion, the user of handheld communication device 110 can easily monitor battery life of one or more wireless devices 120 and charge them when necessary—such as prior to a game or other use of protective headgear 30. While battery life is described above in a pull fashion, a low battery indication from a wireless device 120 can also be pushed to the adjunct device 100, even in circumstances where other event data is pulled from the wireless device 120.

In a further example, the wireless device 120 can emit a location beacon or other signal in response to the polling signal 112 to aid the user of handheld communication device 120 in locating the protective headgear 30. In this embodiment, the protective headgear monitoring application of handheld communication device 110 can include an equipment location software module that, for example presents a special screen that allows the user to monitor the signal strength and/or the directionality of the location signal, to assist the user in homing in on the location of the protective headgear 30. In this embodiment, the wireless device 120, adjunct device 100 and/or handheld communication device 100 includes one or more of the functions and features described in the U.S. Published Application number 2011/021047, entitled "SYSTEM AND WIRELESS DEVICE FOR LOCATING A REMOTE OBJECT", the contents of which are incorporated herein by reference thereto.

Figure 14:
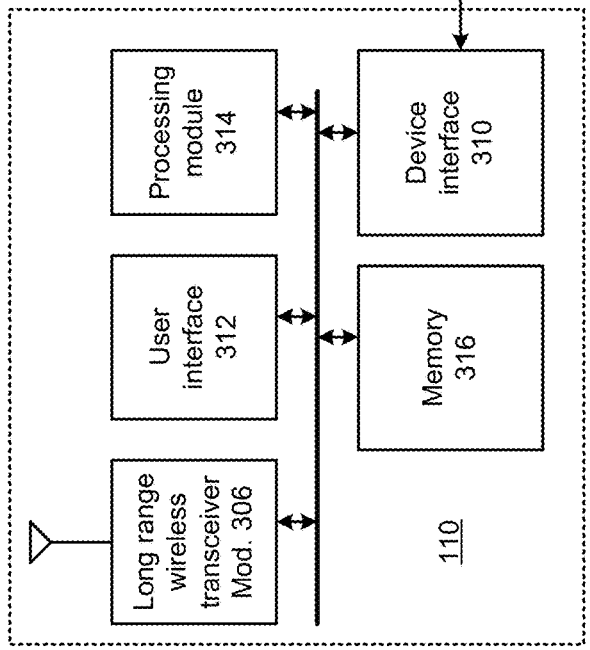
FIG. 14 presents a schematic block diagram of a handheld wireless device 110 in accordance with an embodiment of the present invention.

FIG. 14 presents a schematic block diagram of a handheld wireless device 110 in accordance with an embodiment of the present invention. Handheld communication device 110 includes long range wireless transceiver module 306, such as a wireless telephony receiver for communicating voice and/or data signals in conjunction with a handheld communication device network, wireless local area network or other wireless network. Handheld communication device 110 also includes a device interface 310 for connecting to the adjunct device 100 on either a wired or wireless basis, as previously described. In particular, the device interface 310 includes a communication port that receives the event data 16, 16'... from one or more wireless devices 120 coupled to one or more protective headgear 30, 30'... via an adjunct device 100 connected to the communication port.

In addition, handheld communication device 300 includes a user interface 312 that include one or more pushbuttons such as a keypad or other buttons, a touch screen or other display screen, a microphone, speaker, headphone port or other audio port, a thumbwheel, touch pad and/or other user interface device. User interface 312 includes the user interface devices ascribed to handheld communication device 110.

Handheld communication device 110 includes a processing module 314 that operates in conjunction with memory 316 to execute a plurality of applications including a wireless telephony application and other general applications of the handheld communication device and other specific applications such as the protective headgear monitoring described in conjunction with FIGS. 1-13.

The processing module 314 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 316. Note that when the processing module 314 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 316 stores, and the processing module 314 executes, operational instructions corresponding to at least some of the steps and/or functions illustrated herein.

The memory module 316 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of handheld communication device 110 are shown as being coupled by a particular bus structure, other architectures are likewise possible that include additional data busses and/or direct connectivity between components. Handheld communication device 110 can include additional components that are not expressly shown.

As previously described, event data 16 is generated by wireless device 120 in response to an impact to the protective headgear 30. The event data 16 is transmitted to the adjunct device 100 that transfers the event data 16 to the handheld communication device 110, either wirelessly or via the communication port of the handheld communication device 110. The handheld communication device 110 executes an application to further process the event data 16 to, for example, display a simulation of the head and/or brain of the wearer of the protective headgear 30 as a result of the impact. Further details regarding the simulation of the impact event are presented in conjunction with FIG. 15 that follows.

Figure 15:
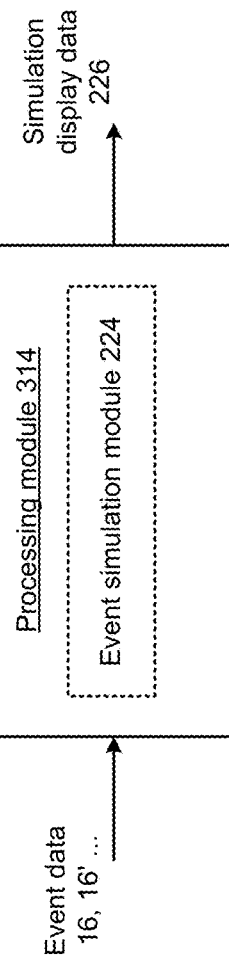
FIG. 15 presents a schematic block diagram of a processing module 314 in accordance with an embodiment of the present invention.

FIG. 15 presents a schematic block diagram of a processing module 314 in accordance with an embodiment of the present invention. In particular processing module 314 executes an event simulation module that processes the event data (16, 16' . . . ) to generate simulation display data 226 that animates the impact to the protective headgear 30. The user interface 312 includes a display device that displays the simulation display data 226. The event simulation module can be included in the protective headgear monitoring application executed by processing module 314 of the handheld communication device 110. The protective headgear monitoring application can be implemented as an article of manufacture that includes a computer readable medium or as other instructions that, when executed by a processing device cause the processing device to implement the functions described herein in conjunction with the other components of the handheld communication device 110. As previously described the protective headgear monitoring application can be an "app" that is downloaded to the handheld communication device 110 via the long range wireless transceiver module 306, a wireless local area network connection or other wired or wireless link.

In an embodiment of the present invention, the event simulation module 224 models a human head that simulates the head of the wearer of the protective headgear (30, 30' . . . ), the shock absorbing capabilities of the protective headgear (30, 30' . . . ) a human skull and/or brain that simulates the skull and brain of the wearer of the protective headgear (30, 30' . . . ). For example, the event simulation module 224 can implement a bulk system model, a lumped parameter system module or other model that accounts for the mass of the head and how its movement is constrained by the joints and musculature the neck. This model allows the event simulation module to account for the way forces and movements are distributed in a bulk way; showing for example, how energy is dissipated over the surface of the brain. The event simulation module can further include a second, more complex model, such as a finite element model or a distributed parameter model that simulates sub-surface displacements/injury to brain matter. In this fashion, power, velocity and/or displacement data either received as event data 16 or calculated locally in response to event data 16 that includes sensor data 206 corresponding to an event can be used to simulate the impact.

In an embodiment of the present invention, the simulation display data 226 includes graphics and video animation to visually communicate the nature and potential extent of the injury caused by an impact event. A depiction of the brain can be animated, showing the entire impact event. Power, velocity and/or other event data 16 are used to drive the animation, while a color map is applied to the surface of the brain to indicate points of high energy dissipation. The simulation display data 226 can also show possible brain impact with the skull as well as the deformation of brain matter as predicted by the second, more complex model.

In addition, to simply providing an animation, the event simulation module 224 can generate an alarm event signal as part of the simulation display data 226. This alarm event signal can be generated when the event simulation module 224 either receives event data 16 regarding any impact that indicates the alarm event directly, or alternatively when the event simulation module 224 determines that an impact has occurred with sufficient force as a cause a possible injury. For example the event simulation module 224 can compare a peak power to an injury threshold and generate the alarm event signal when the peak power exceeds an injury threshold. In the alternative, the event simulation module can analyze the results of the brain or head modeling and determine a potential injury situation and trigger the alarm event signal in response to such a determination. The alarm event signal is used to trigger a visual alarm such as a warning light, banner display or display message and/or an audible alarm such as a tone, alarm sound, buzzer or other audible warning indicator. While the description above includes a single threshold, multiple thresholds can be employed to determine alarm events of greater or lesser severity. Different responses to the alarm event signal can be employed, based on the severity of the alarm event.

In addition to generating a local alarm, the alarm event signal, the event data (16, 16' . . . ) and/or the simulation display data 226 can be sent by the handheld communication device 110 to a remote monitoring station via the wireless telephony transceiver module 206. In this fashion, the event data (16, 16' . . . ) and/or the simulation display data 226 can be subjected to further analysis at a remote facility such as hospital, doctor's office or other remote diagnosis or treatment facility in conjunction with the diagnosis and treatment of the wearer of the protective headgear (30, 30' . . . ) that was the subject of the impact. It should be noted that the transmission of a wireless signal including the event data (16, 16' . . . ) and/or the simulation display data 226 can be either triggered automatically in response to the alarm event signal or triggered manually in response to an indication of the user of the handheld communication device 110, via interaction with the user interface 312.

Figure 16:
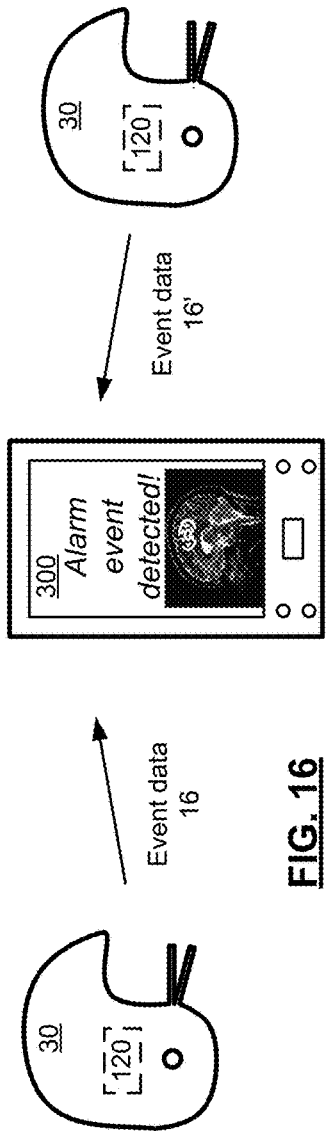
FIG. 16 presents a pictorial representation of a system for monitoring protective headgear in accordance with an embodiment of the present invention.

FIG. 16 presents a pictorial representation of a system for monitoring protective headgear in accordance with an embodiment of the present invention. While many of the prior descriptions of the present invention contained herein focus on functions and features ascribed to an adjunct device operating in conjunction with a handheld communication device, the functions and features of the adjunct device/handheld communication device combination can be implemented in an enhanced handheld communication device that includes structure and functionality drawn from an adjunct device, such as adjunct devices 100. Handheld communication device 300 presents such a device that includes a handheld communication device portion having the standard components of a handheld communication device and an adjunct portion that adds the components necessary to provide the additional functions and features of the adjunct device 100. In summary, handheld communication device 300 includes the structure and functionality of any of the embodiments of handheld communication device 110 and adjunct device 100 to interact with one or more wireless devices 120 included in one more articles or protective headgear 30.

Figure 17:
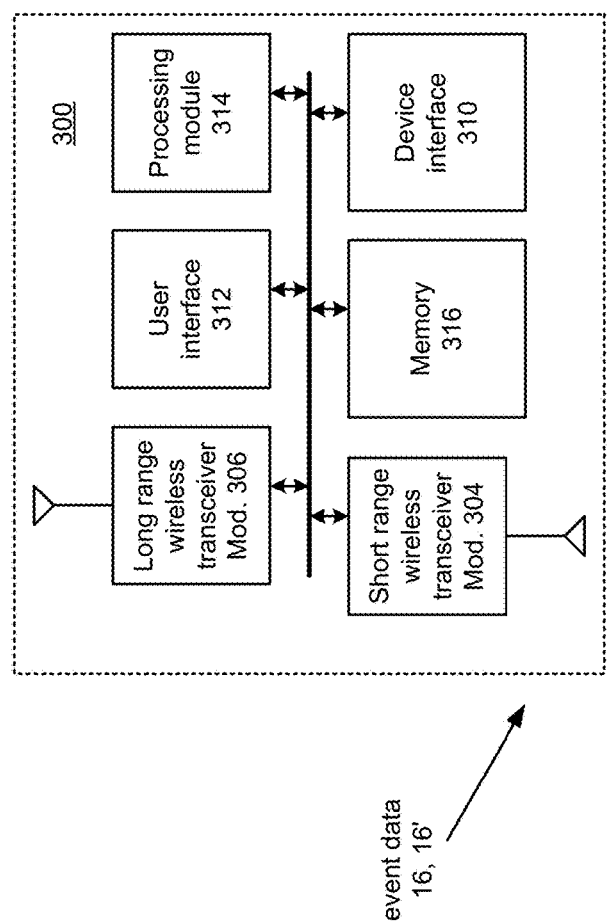
FIG. 17 presents a schematic block diagram of a handheld wireless device 300 in accordance with an embodiment of the present invention.

FIG. 17 presents a schematic block diagram of a handheld wireless device 300 in accordance with an embodiment of the present invention. Handheld communication device includes similar elements to handheld communication device 110 that are referred to by common reference numerals. In addition, handheld communication device 300 includes a short range wireless transceiver module 304 that operates in a similar fashion to short range wireless transceiver 140 to provide a device interface to interact with one or more wireless devices 120, to receive event data (16, 16' . . . ) and to transfer this event data to processing module 314 for further analysis.

Figure 18:
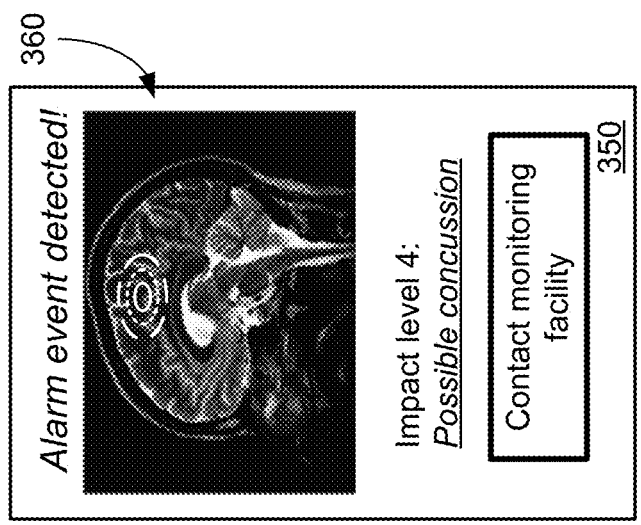
FIG. 18 presents a pictorial representation of a screen display 350 in accordance with an embodiment of the present invention.

FIG. 18 presents a pictorial representation of a screen display 350 in accordance with an embodiment of the present invention. In particular, screen display 350 is shown of simulation display data 226 in accordance with a particular example. In this example, screen display 250 includes a frame 360 of video animation that visually communicates the nature and potential extent of the injury caused by an impact event. A depiction of the brain and skull is animated, showing a particular video frame of the entire impact event. A series of graphical overlays outline regions of high energy dissipation on the surface of or internal to the brain. In this diagram different regions are indicates as to the intensity of energy dissipation based on lines of different styles, however, regions of different colors can likewise be used to provide greater visual contrast.

In addition to the video animation, the simulation display data 226 provides a visual indication of an alarm event by displaying the text, "Alarm event detected!" and further an indication of the level of impact and its possible effect, "Impact level 4: Possible concussion". An interactive portion of the screen display 350 can be selected by the user to initiate the process of contacting a monitoring facility such as hospital, doctor's office or other remote diagnosis or treatment facility.

Figure 19:
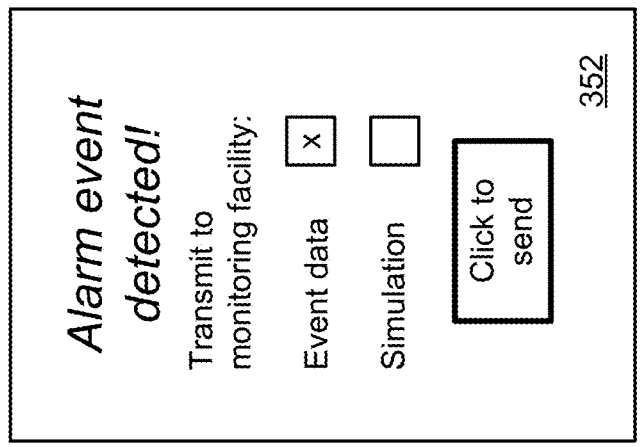
FIG. 19 presents a pictorial representation of a screen display 352 in accordance with an embodiment of the present invention.

FIG. 19 presents a pictorial representation of a screen display 352 in accordance with an embodiment of the present invention. In particular, an example of a follow-up screen is presented in response to the selection by the user to contact a monitoring facility described in conjunction with FIG. 18. In particular, screen display 352 allows the user to select the type of information to be sent to the monitoring facility. In the example shown, the user can select event data, such as event data (16, 16' . . . ) and/or a full simulation, such as simulation display data 226 or other simulation results to be transmitted to the remote facility. While not expressly shown, the event data and simulation data can be accompanied by information that identifies the user of the handheld communication device, the wearer of the protective headgear that was the subject of the impact event, other identifying data such as address information, physician information, medical insurance information and/ or other data. An interactive portion of the screen display 352 can be selected by the user to either store the selected data or used to initiate the transmission of the selected data to a monitoring facility such as hospital, doctor's office or other remote diagnosis or treatment facility.

FIG. 20 presents a flowchart representation of a method in accordance with an embodiment of the present invention. In particular, a method is shown for use in conjunction with one or more functions and features described in conjunction with FIGS. 1-19. In step 400, sensor data is generated, via a sensor module, in response to motion of protective headgear, wherein the sensor module includes an accelerometer and a gyroscope and wherein the sensor data includes linear acceleration data and rotational velocity data. In step 402, event data is generated in response to the sensor data. In step 404, a wireless signal that includes the event data is transmitted via a short-range wireless transmitter.

In an embodiment of the present invention, the wireless signal is transmitted to an adjunct device that is coupled to a handheld communication device for processing of the event data by the handheld communication device. The accelerometer responds to acceleration of the protective headgear along a plurality of axes and the linear acceleration data indicates the acceleration of the protective headgear along the plurality of axes. In addition, the gyroscope responds to angular velocities of the protective headgear along a plurality of axes and the rotational velocity data indicates the velocity of the protective headgear along the plurality of axes.

FIG. 21 presents a flowchart representation of a method in accordance with an embodiment of the present invention. In particular, a method is shown for use in conjunction with one or more functions and features described in conjunction with FIGS. 1-20. In step 410, sensor data is generated, via a sensor module, in response to motion of protective headgear. In step 412, the sensor data is analyzed to detect an event in the sensor data. In step 414, event data is generated in response to the sensor data when triggered by detection of the event in the sensor data. In step 416, a wireless signal that includes the event data is transmitted via a short-range wireless transmitter.

In an embodiment of the present invention, the wireless signal is transmitted to an adjunct device that is coupled to a handheld communication device for processing of the event data by the handheld communication device. Step 412 can include generating aggregate acceleration data from the sensor data; comparing the aggregate acceleration data to an acceleration threshold; and determining an event window that indicates an event time period based on the comparing of the aggregate acceleration data to the acceleration threshold. Step 414 can be triggered based on the event window, such as after the event window ends and the event data can be generated in step 414 in response to the sensor data corresponding to the event window.

FIG. 22 presents a flowchart representation of a method in accordance with an embodiment of the present invention. In particular, a method is shown for use in conjunction with one or more functions and features described in conjunction with FIGS. 1-21. In step 420, sensor data that includes acceleration data is generated via a sensor module, in response to an impact to the protective headgear. In step 422, sensor data is analyzed to generate power data that represents power of impact to the protective headgear. In step 424, event data is generated that includes the power data. In step 426, a wireless signal that includes the event data is transmitted, via a short-range wireless transmitter.

In an embodiment of the present invention, the wireless signal is transmitted to an adjunct device that is coupled to a handheld communication device for processing of the event data by the handheld communication device. Step 422 can include generating velocity data and the event data is generated in step 424 to further include the velocity data. Step 422 can include generating displacement data and the event data is generated in step 424 to further include the displacement data.

FIG. 23 presents a flowchart representation of a method in accordance with an embodiment of the present invention. In particular, a method is shown for use in conjunction with one or more functions and features described in conjunction with FIGS. 1-22. In step 430, a wake-up signal and sensor data that includes acceleration data are generated, via a sensor module, in response to an impact to the protective headgear. In step 432, a short-range transmitter and a device processing module are selectively powered in response to the wake-up signal. In step 434, event data is generated in response to the sensor data via the device processing module, when the device processing module is selectively powered. In step 436, a wireless signal that includes the event data is transmitted, via the short-range wireless transmitter, when the short-range transmitter is selectively powered.

In an embodiment of the present invention, the wireless signal is transmitted to an adjunct device that is coupled to a handheld communication device for processing of the event data by the handheld communication device. The first sensor data can be generated in response to the wake-up signal. The first wake-up signal can be generated when an acceleration signal compares favorably to a first signal threshold or by a kinetic sensor, etc.

FIG. 24 presents a flowchart representation of a method in accordance with an embodiment of the present invention. In particular, a method is shown for use in conjunction with one or more functions and features described in conjunction with FIGS. 1-23. In step 440, first event data that includes power data that represents power of impact to the protective headgear is received, via a device interface of the handheld communication device. In step 442, the event data is processed to generate simulation display data that animates the impact to the protective headgear. In step 444, the simulation display data is displayed via a display device of the handheld communication device.

In an embodiment of the present invention, the device interface includes a communication port that receives the event data from a first wireless device coupled to the protective headgear via an adjunct device connected to the communication port. The device interface can includes an RF transceiver that receives the event data from a first wireless device coupled to the protective headgear. The event data can be received from a plurality of wireless devices coupled to the protective headgear. The event data can further include velocity data that represents velocity of impact to the protective headgear and/or displacement data that represents displacement of impact to the protective headgear.

Step 442 can include modeling at least one of: shock absorbing capabilities of the protective headgear, a human head that simulates a head of a wearer of the protective headgear, and a human brain that simulates a brain of the wearer of the protective headgear. The simulation display data can animate the impact to the protective headgear by animating at least one of: the protective headgear, the human head, the human skull and the human brain.

The method can further include generating an alarm event signal in response to the event data and presenting, via the user interface, at least one of: an audible alarm or a visual alarm in response to the alarm event signal. In addition, the method can include transmitting, via a wireless telephony transceiver of the handheld communication device and in response to the alarm event signal, at least one of: the event data, and the simulation display data.

Figure 25:
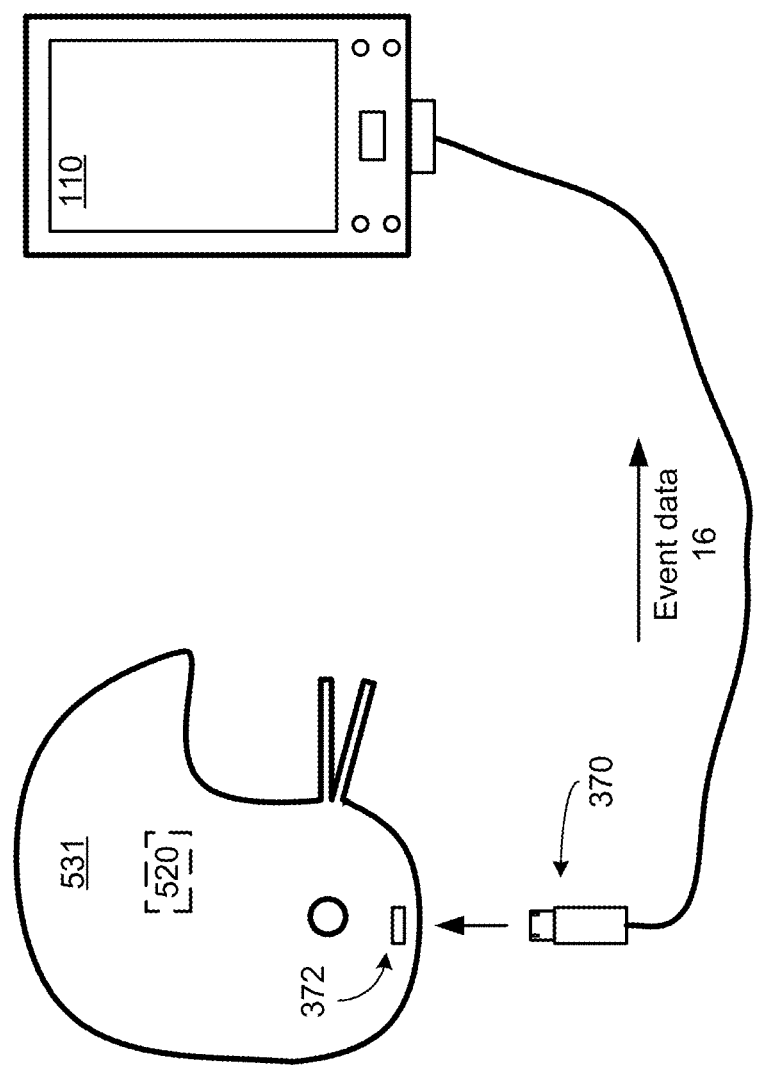
FIG. 25 presents a pictorial representation of a system for monitoring protective headgear in accordance with an embodiment of the present invention.

FIG. 25 presents a pictorial representation of a system for monitoring protective headgear in accordance with an embodiment of the present invention. In particular, a system is shown for use in monitoring protective headgear 531, such as the football helmet shown, or a hat, headband, mouth guard or other headgear used in sports, a motorcycle or driving helmet, other headgear and helmets worn by public safety or military personnel or other headgear or helmets or any other protective headgear. Instead of having one or more wireless devices 120 or 121, protective headgear 531 includes device 520 that operates in a similar fashion to wireless devices 120 or 121 to generate event data 16. In pertinent part however, instead of having a wireless link to a monitoring device, the device 520 includes a wired device interface having a connection port 372 that can be coupled to a monitoring device, such as the handheld wireless device 110 via the cable 370.

In operation, event data 16 is generated by device 520 in response to an impact to the protective headgear 531 and stored for retrieval via the monitoring device. A monitoring device, such as handheld communication device 110, or other monitoring device such as a personal computer, tablet, or other processing device can be coupled to the protective headgear by, for example, plugging a plug of the cable 370 into a jack included in connection port 372. When connected, the event data 16 can be sent via the cable 370 to the monitoring device. As previously discussed, the handheld communication device 110 or other monitoring device executes an application to receive and further process the event data 16 to, for example, display a simulation of the head and/or brain of the wearer of the protective headgear 30 as a result of the impact. This application can include instructions, that, when executed by a processor, such as processing module 314, cause the processor to perform the steps associated with the application. These instructions can be stored on an article of manufacture that includes a computer readable storage medium such as a disk, memory card, memory stick, memory or other memory device.

Figure 26:
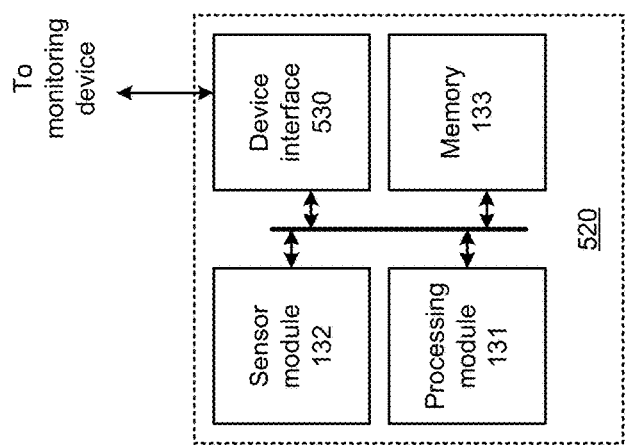
FIG. 26 presents a schematic block diagram of a device 520 in accordance with an embodiment of the present invention.

FIG. 26 presents a schematic block diagram of a device 520 in accordance with an embodiment of the present invention. In particular, device 520 includes common elements to wireless device 120 or 121 that are referred to by common reference numerals. Instead of having a short range wireless transceiver 130, the device 520 includes a device interface 530 that is coupleable to a monitoring device and that sends the event data 16 to the monitoring device when the device interface 530 is coupled to the monitoring device.

Event data 16 is generated by sensor module 132 and processing device 131 in response to an impact to the protective headgear 531 and stored in memory 133 for retrieval via the monitoring device. When the monitoring device is connected, the event data 16 can be sent via the cable 370 to the monitoring device. In an embodiment of the present invention, the device interface 530 includes a jack that is coupleable to the monitoring device via a standardized cable, such as a universal serial bus (USB) cable, a Firewire cable or other cable having a plug that mates with the jack. It should be noted that sensor module can include one sensor modules with one or more sensors or a plurality of sensor modules placed at different points on the protective headgear 531. In another embodiment, the device interface 530 includes a one connector interface such as a contact pad, contact point, one connector jack or other one connector interface.

Whether the device interface 530 is implemented via a one connector or a multiwire interface the device interface 530 can include a sensor that detects coupling to the monitoring device. When the device interface 530 detects that the monitoring device is coupled to the device interface, the device interface 530 automatically initiates transmission of event data to the monitoring device in response to the detection of the coupling by the monitoring device. The device interface can include a jack with an integrated switch, a button or other device that provides an open circuit or a closed circuit when the monitoring device is coupled to the device interface 530. In the alternative, the device interface can include a contact sensor, a proximity sensor or other sensor that senses that the monitoring device is coupled to the device interface and generates a coupling signal that is used by the device interface 530 to trigger the transmission of the event data to the monitoring device via the device interface.

Figure 27:
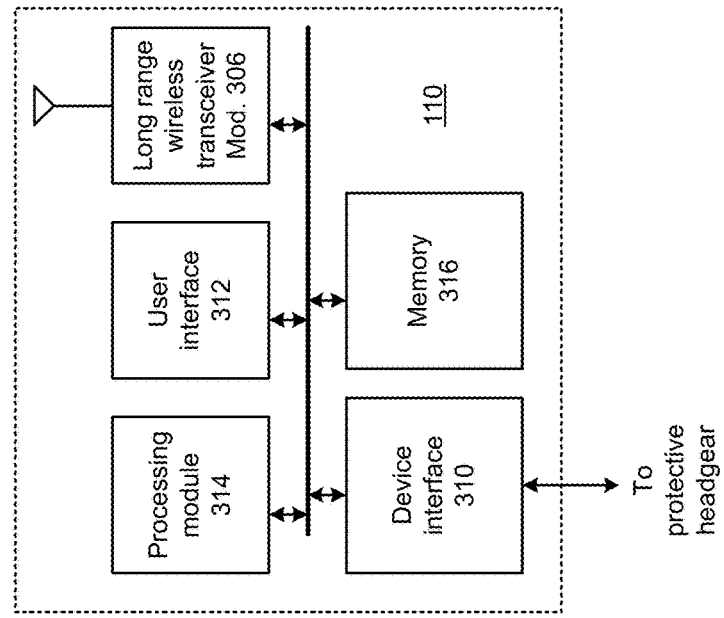
FIG. 27 presents a schematic block diagram of a handheld communication device 110 in accordance with an embodiment of the present invention.

FIG. 27 presents a schematic block diagram of a handheld communication device 110 in accordance with an embodiment of the present invention. In particular, handheld communication device 110 operates as a monitoring device for receiving event data 16 from protective headgear, such as protective headgear 531.

As discussed in conjunction with FIG. 14, handheld communication device 110 includes long range wireless transceiver module 306, such as a wireless telephony receiver for communicating voice and/or data signals in conjunction with a handheld communication device network, wireless local area network or other wireless network. Handheld communication device 110 also includes a device interface 310, but instead of receiving the event data 16 via an adjunct device, the device interface 310 in this embodiment connects to the connection port 372 of protective headgear 531. In particular, the device interface 310 includes a communication port such as a USB port, Firewire port or other port that either retrieves event data 16 from memory 133 of device 520 or otherwise receives the event data 16 from one or more devices 520 when coupled to one or more protective headgear 531.

In addition, handheld communication device 300 includes a user interface 312 that include one or more pushbuttons such as a keypad or other buttons, a touch screen or other display screen, a microphone, speaker, headphone port or other audio port, a thumbwheel, touch pad and/or other user interface devices ascribed to handheld communication device 110.

Figure 28:
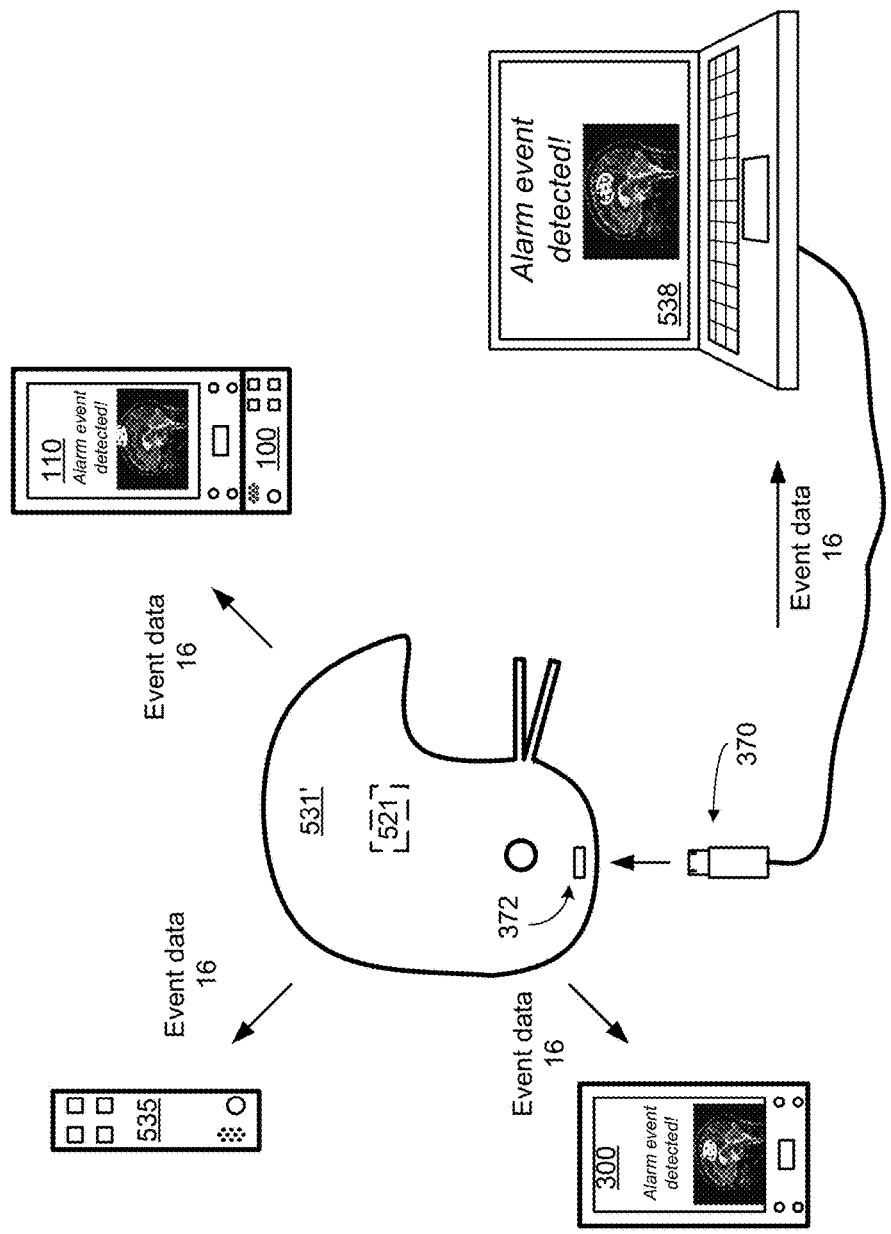
FIG. 28 presents a pictorial representation of a system for monitoring protective headgear in accordance with an embodiment of the present invention.

FIG. 28 presents a pictorial representation of a system for monitoring protective headgear in accordance with an embodiment of the present invention. In particular, a system is shown for use in monitoring protective headgear 531', such as the football helmet shown, or a hat, headband, mouth guard or other headgear used in sports, a motorcycle or driving helmet, other headgear and helmets worn by public safety or military personnel or other headgear or helmets or any other protective headgear. The protective headgear 531 includes device 521 that operates in a similar fashion to wireless devices 120 or 121 to generate event data 16 and includes both a wireless transceiver such as short range wireless transceiver 130 and further a wired device interface having a connection port 372 that can be coupled to a monitoring device, such as the handheld wireless device 110 via the cable 370. In this fashion, event data can be sent on either a wireless basis to wireless device 535, to handheld wireless device 110 via adjunct device 100, to a wireless device 300 or to a monitoring device such as personal computer 538.

In operation, event data 16 is generated by device 521 in response to an impact to the protective headgear 531. The event data 16 is transmitted to wireless device 535 and adjunct device 100 on either a push or pull basis and also is stored for retrieval via the monitoring device. When a monitoring device, such as personal computer 538, is connected to the protective headgear 531', the event data 16 can be transmitted via the cable 370. In this case the personal computer 538 operates in a similar fashion to handheld device 110 to execute an application to further process the event data 16 to, for example, display a simulation of the head and/or brain of the wearer of the protective headgear 30 as a result of the impact.

FIG. 29 presents a schematic block diagram of a wireless device 521 in accordance with an embodiment of the present invention. In particular, a wireless device 521 is presented that includes common elements of wireless device 120, 121 and device 520 that are referred to by common reference numerals. The wireless device 52, in one mode or operation, operates in a similar fashion to wireless devices 120 or 121 to transmit event data 16 via short range wireless transceiver 130 on either a push basis or in response to a polling signal.

In addition, event data 16 can be stored in memory 133 and retrieved when coupled to a monitoring device via device interface 530.

It should be noted that wireless device 521 includes a battery 522 that provides power for the short range wireless transceiver, processing module 131, the sensor module 132 or 232, the memory 133 and the device interface 530. In an embodiment of the present invention the status of battery 522 is monitored via power management module of sensor module 232 and processing module 131. When a low battery condition is detected, the short range wireless transceiver 130 can be disabled and powered off in order to save power and the event data 16 stored memory 133 can still be retrieved via a monitoring device coupled to device interface 530.

FIG. 30 presents a schematic block diagram of a wireless device 535 in accordance with an embodiment of the present invention. As previously discussed, event data 16 can include an alarm indication. This alarm data can be generated in a failsafe mode of operation or routinely as part of event data 16. In particular this alarm data can be received and used by wireless devices to generate a detectable alert signal in response to the alarm data to assist users in monitoring the protective headgear. Wireless device 535 is an example of a device that receives and responds to this alarm data. In particular, unlike the monitoring devices such as handheld communication devices 110, or 300 or personal computer 538, the wireless device 535 can be designed and implemented with more limited functionality—to indicate an alarm event in a detectable fashion, without necessarily performing any processing or simulation based on the other event data 16.

Wireless device 535 includes a short-range wireless transceiver 540 such as short-range wireless transceiver 130 that includes a receiver that receives alarm data included in event data 16 in response to an alarm event at the protective headgear, such a protective headgear 30, 31, 531, 531', etc. The short-range wireless transceiver 540 can be implemented via a transceiver that operates in conjunction with a communication standard such as 802.11, Bluetooth, 802.15.4 standard running a ZigBee or other protocol stack, ultra-wideband, Wimax or other standard short or medium range communication protocol, or other protocol. User interface 542 can contain one or more push buttons, a sound emitter, light emitter, a touch screen or other display screen, a thumb wheel, trackball, and/or other user interface devices.

The processing module 541 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 543. Note that when the processing module 541 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 543 stores, and the processing module 541 executes, operational instructions corresponding to at least some of the steps and/or functions illustrated herein.

The memory module 543 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of wireless device 535 are shown as being coupled by a particular bus structure, other architectures are likewise possible that include additional data busses and/or direct connectivity between components. Wireless device 535 can include additional components that are not expressly shown.

In operation, event data 16 is received by short range wireless transceiver 540. Processing device processes the alarm data and triggers the user interface device 542 to emit a detectable alert signal in response to the reception of the alarm data to assist the user in the monitoring of the protective headgear. This detectable alert signal can be a flashing light, message display or other visual alarm, an audible tone, buzzer or other audible alarm, a vibration or other tactile alarm or other alarm signal.

While not expressly shown, wireless device 535 can include a replaceable battery for powering the components of wireless device 535. In the embodiment shown, wireless device 535 includes a battery 544 for powering the components of wireless device 535 that is rechargeable via an external charging port 546 based on an external power source. In an embodiment of the present invention, the charging port 546 operates in accordance with a USB interface or couples to another source of electrical power for charging the battery in a traditional fashion. In another embodiment, the charging port 546 operates to charge the battery by harvesting energy from an external source, and wherein the external energy source includes one of: a magnetic power source, a radio frequency power source, a mechanical power source, and a solar power source. In these embodiments, the charging part 546 can include a coil, antenna, solar cell, piezoelectric element, capacitor and/or circuit for generating and/or storing power from a magnetic or radio frequency source, a solar power source or a kinetic or other mechanical source of power.

In an embodiment of the present invention, the processing module 541 is coupled to monitor the status of battery 544. The short range wireless transceiver 540 can receive a polling signal, such as a polling signal 112. Wireless device 535 can operate similarly to wireless device 120 as described in conjunction with FIG. 14 to monitor its remaining battery life and transmit battery life data such as battery charge status or other status information to an adjunct device 100 in response to the polling signal 112. In this fashion, the user of handheld communication device 110 can easily monitor battery life of one or more wireless devices 535 and charge them when necessary—such as prior to a game or other use of protective headgear 30. While battery life is described above as being obtained in a pull fashion, a low battery indication from a wireless device 535 can also be pushed to the adjunct device 100.

In an embodiment of the present invention the short range wireless transceiver 540 is paired with the short range wireless transceiver 130 of the protective headgear via a pairing procedure, such as a Bluetooth pairing procedure, a 802.15.4 standard running a ZigBee or other protocol stack pairing procedure, an 802.11 association or other similar pairing or association that identifies the wireless transceivers to one another to facilitate communication between these two devices, either directly or indirectly. It should also be noted that the wireless device 535 can be paired to a bridge device and can receive alarm data from one or more protective headgear indirectly, through the bridge device. The wireless device 535 can be paired with a plurality of protective headgear warn by different wearers in order to emit a detectable alarm if any of the protective headgear emits an alarm indication. In this embodiment, the alarm data can include a unique or pseudo-unique indicator of the particular protective headgear and the wireless device 535 can analyze this indicator to indicate the particular one or ones of the plurality of protective headgear that transmitted the alarm indication.

Figure 31:
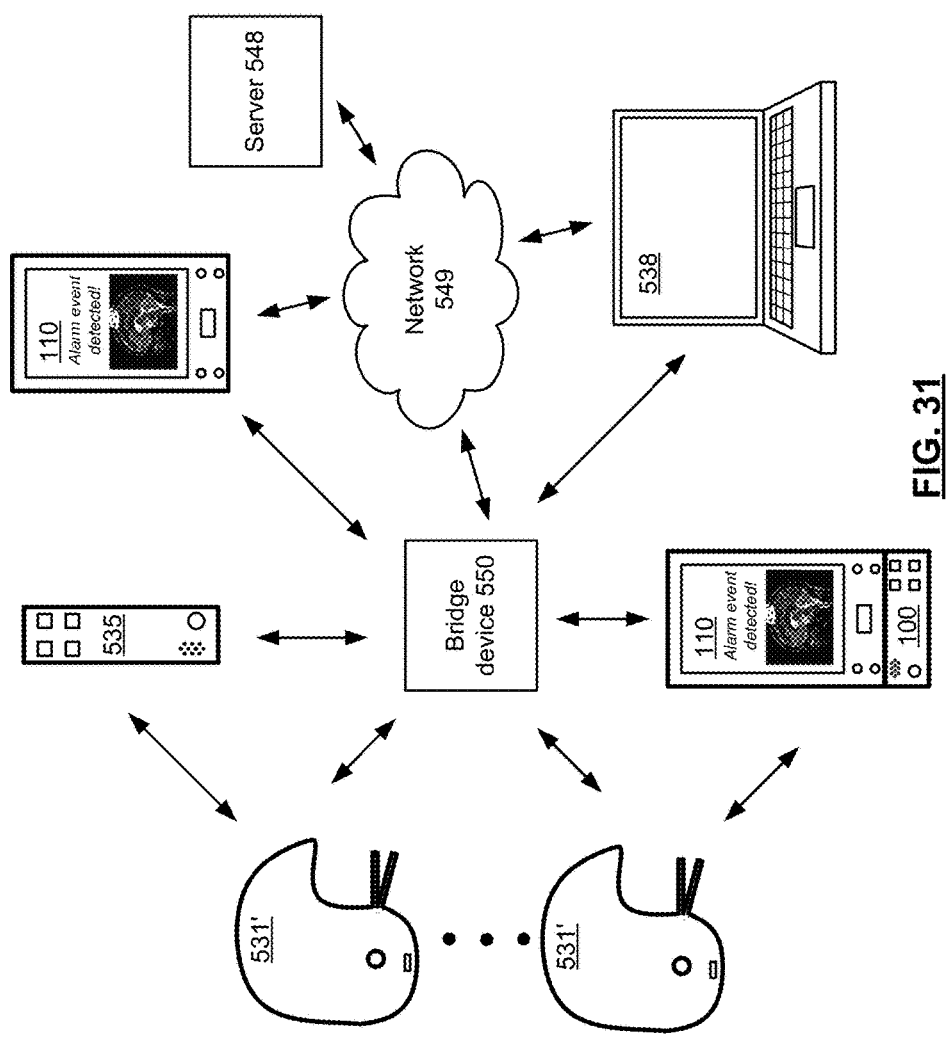
FIG. 31 presents a pictorial representation of a system for monitoring protective headgear in accordance with an embodiment of the present invention.

FIG. 31 presents a pictorial representation of a system for monitoring protective headgear in accordance with an embodiment of the present invention. While prior descriptions have focused mainly on the direct communication of event data 16 from protective headgear, such as protective headgear 30, 31, 531, 531' etc. to a device such as wireless device 535, handheld communication device 300, a monitoring device such as personal computer 538 or the device combination of handheld wireless device 110 and adjunct device 100, the present embodiment includes a bridge device 550 that communicates event data from one or more protective headgear, such as protective headgear 531' to one or more other devices.

In operation, the bridge device includes a short range wireless transceiver that can be paired with, and receive event data 16 from one or more articles of protective headgear 531'. The bridge device retransmits the event data 16 on either a wired or wireless basis to monitoring devices such as handheld communication device 110, personal computer 538 such as a laptop, notebook, tablet, pad, or other computer. In particular, the bridge device can include a second wireless transceiver such as a 802.11, WIMAX, 3G, 4G or other wireless telephony transceiver of other wireless transceiver to communicate the event data 16 to a monitoring device, either directly or via a wireless network such as a wireless telephone network or other wireless data network. In addition, the bridge device can include a network card or other network interface such as an Ethernet interface or USB interface that couples the bridge device to a wide area data network 549 such as the Internet. In this fashion, the event data 16 can be stored on a network server such as 548 where it can be retrieved by a monitoring device or can be transmitted via the network 549 to one or more monitoring devices.

In a further mode of operation, the bridge device 550 acts as a repeater to receive event data 16 from one or more articles of protective headgear 531' and to retransmit the event data 16 to a device such as wireless device 535, handheld communication device 300 or adjunct device 100 that may otherwise be out of range of the protective headgear 531'. In an embodiment of the present invention, the bridge device 550 communicates with the protective headgear via non-RF communications to avoid the use of RF communications too close to the brain. In this embodiment, optical, infrared or magnetic short range wireless transceivers are used in the protective headgear and the bridge device 550 to communicate with each other. In this fashion, the bridge device can be placed at the belt of a wearer or at some other point in proximity to the wearer. The bridge device 550 can include an RF transceiver for communicating with other devices.

It should be noted that the various functions of processing, storing and displaying event data, simulations, alarms, status information and other data associated with the protective headgear 531' can be distributed or duplicated among various devices in a network configuration, cloud configuration, or other distributed processing and/or storage configuration of devices in communication, either directly or indirectly.

Figure 32:
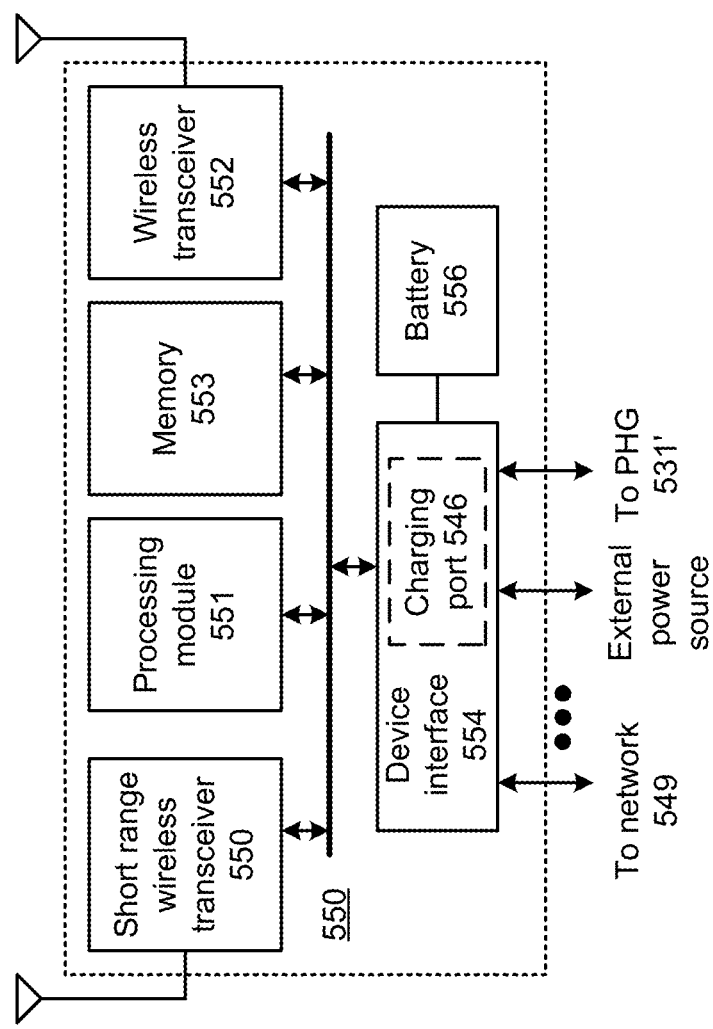
FIG. 32 presents a schematic block diagram of a bridge device 550 in accordance with an embodiment of the present invention.

FIG. 32 presents a schematic block diagram of a bridge device 550 in accordance with an embodiment of the present invention. Bridge device 550 includes short range wireless transceiver 550, such as short range wireless transceiver 130 or 140, that receives event data, such as event data 16 via an incoming RF signal from the protective headgear in response to an impact event at the protective headgear. The short range wireless transmitter 550 can be paired with the articles of protective headgear 531' and optionally with one or more other devices such as wireless device 535 and adjunct device 110.

The incoming RF signal is formatted in accordance with a first wireless protocol, such as 802.15.4 standard running a ZigBee or other protocol stack, Bluetooth, etc. A second RF transceiver, such as wireless transceiver 552, that transmits the event data 116 in accordance with a second wireless protocol to a first monitoring device. The second wireless protocol can be a wireless local area network protocol such as an 802.11 protocol, a 3G, 4G or other compatible cellular data protocol, a WIMAX protocol or other wireless protocol that is different from the protocol employed by short range wireless transceiver 130. Bridge device 550 includes a processing module 551 and memory 553 that operate to convert the event data 16 as received in conjunction with first wireless protocol for transmission in conjunction with the second wireless protocol. As discussed in conjunction with FIG. 31, the incoming signal can be a non-RF signal in configurations where the bridge device 550 communicates with the protective headgear via non-RF communications.

The bridge device 550 includes battery for powering the short range wireless transceiver 550, the processing module 551, the wireless transceiver 552, the memory 553, and the device interface 554. The device interface 554 includes a charging port 546 for coupling a power signal from an external power source to charge the battery 556. The device interface optionally includes one or more communication ports such as an Ethernet communication port, a USB port or other wired port for connection to a wide area data network such as network 549 for communication with either server 548 or one or more monitoring devices that are coupled to the network 549.

In an embodiment of the present invention the charging port 546 can include a connector for connecting a power supply. In addition or in the alternative, the device interface 546 can include a USB port that can be coupled either to protective headgear 531' or to a monitoring device, such as handheld wireless device 110 or personal computer 538. In circumstances where an external power supply is coupled to bridge device 550, the USB port can supply power to a device such as handheld communication device 110 or protective headgear 531' coupled thereto. In other configurations, power from a monitoring device such as personal computer 538 can be coupled to the USB port and the USB port can operate as a charging port 546 to charge battery 556 from power received from the personal computer 538.

As discussed in conjunction with FIG. 31, the bridge device 550 optionally acts as a repeater to receive event data 16 from one or more articles of protective headgear 531' and to retransmit the event data 16 to a device such as wireless device 535, handheld communication device 300 or adjunct device 100 that may otherwise be out of range of the protective headgear 531'. In this fashion, short range wireless transceiver 130 operates as both a receiver and as transmitter of event data 16.

In various modes of operation, event data 16 received by bridge device 550 can be sent to the Internet via a wired Ethernet connection r other wires connection, a wireless local area network connection or a wireless telephony network. In addition, event data 16 received by bridge device 550 can be sent to a monitoring device directly via a wireless telephony network, a wireless local area network or via direct wired connection to the bridge device 550.

The processing module 551 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 553. Note that when the processing module 551 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 553 stores, and the processing module 551 executes, operational instructions corresponding to at least some of the steps and/or functions illustrated herein.

The memory module 553 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of bridge device 550 are shown as being coupled by a particular bus structure, other architectures are likewise possible that include additional data busses and/or direct connectivity between components. Bridge device 550 can include additional components that are not expressly shown.

Figure 33:
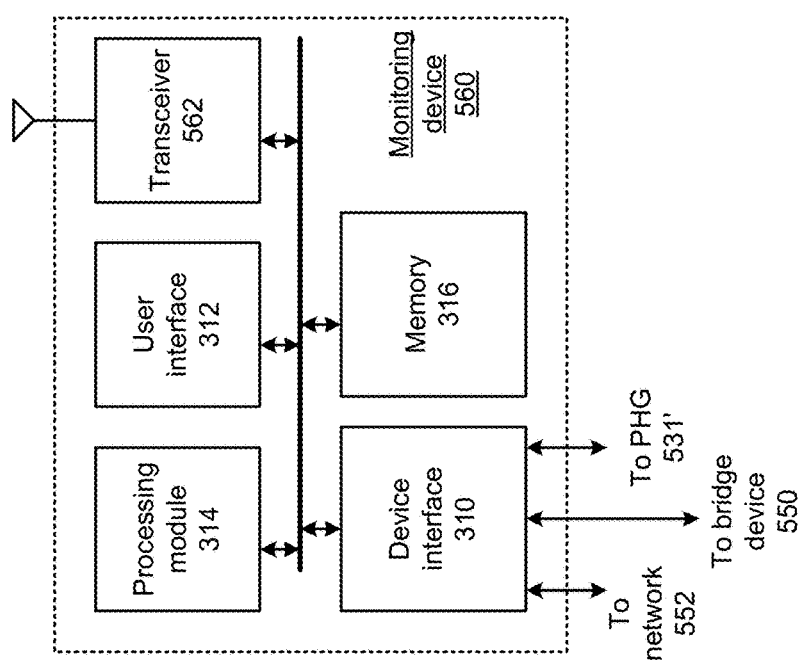
FIG. 33 presents a schematic block diagram of a monitoring device 560 in accordance with an embodiment of the present invention.

FIG. 33 presents a schematic block diagram of a monitoring device 560 in accordance with an embodiment of the present invention. In particular a monitoring device, such as handheld communication device 110 or personal computer 538 is presented. Monitoring device 560 includes a processing device 314, memory 316, and user interface 321 that can operate, as previously described to process event data, such as event data 16 for display and/or retransmission. In pertinent part however, the event data can be received via device interface 310 via network 549 and bridge device 550, via device interface 310 coupled directly to bridge device 550, of via device interface 310 coupled directly to protective headgear 531'.

Monitoring device 560 further includes transceiver 562 such as a local area network transceiver, wireless telephony transceiver or other wireless data transceiver that itself operates as a wireless device interface to either the bridge device 550 or network 549. In this fashion, monitoring device can receive event data 16 directly from bridge device 550 via transceiver 562, indirectly from bridge device 550 through network 549 or via a cellular data network, wireless area network, etc.

Figure 34:
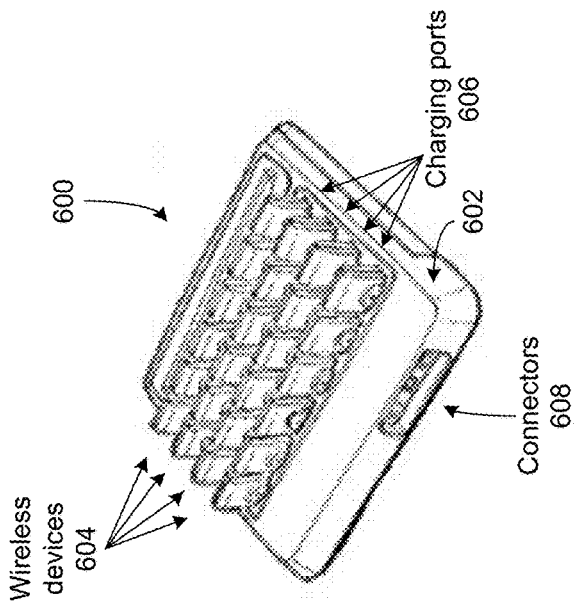
FIG. 34 presents a pictorial representation of a charging device 600 in accordance with an embodiment of the present invention.

FIG. 34 presents a pictorial representation of a charging device 600 in accordance with an embodiment of the present invention. A charging device 600 is shown that include a housing 602 and a plurality of charging ports 606 recessed in the housing 602. Each of the charging ports 606 can accept, and selective couple to one of a plurality of wireless devices 604, such as wireless device 535. When coupled to a wireless device 604, the charging port 606 couples a power signal to the wireless device based on an external power source coupled to the charging device 600 from an external power source such as an external power supply or other power source.

Each of the charging ports 606 can be configured in accordance with a universal serial bus (USB) interface or other interface, depending on the configuration of the wireless devices 604. As shown, the plurality of charging ports are arranged in rows.

Figure 35:
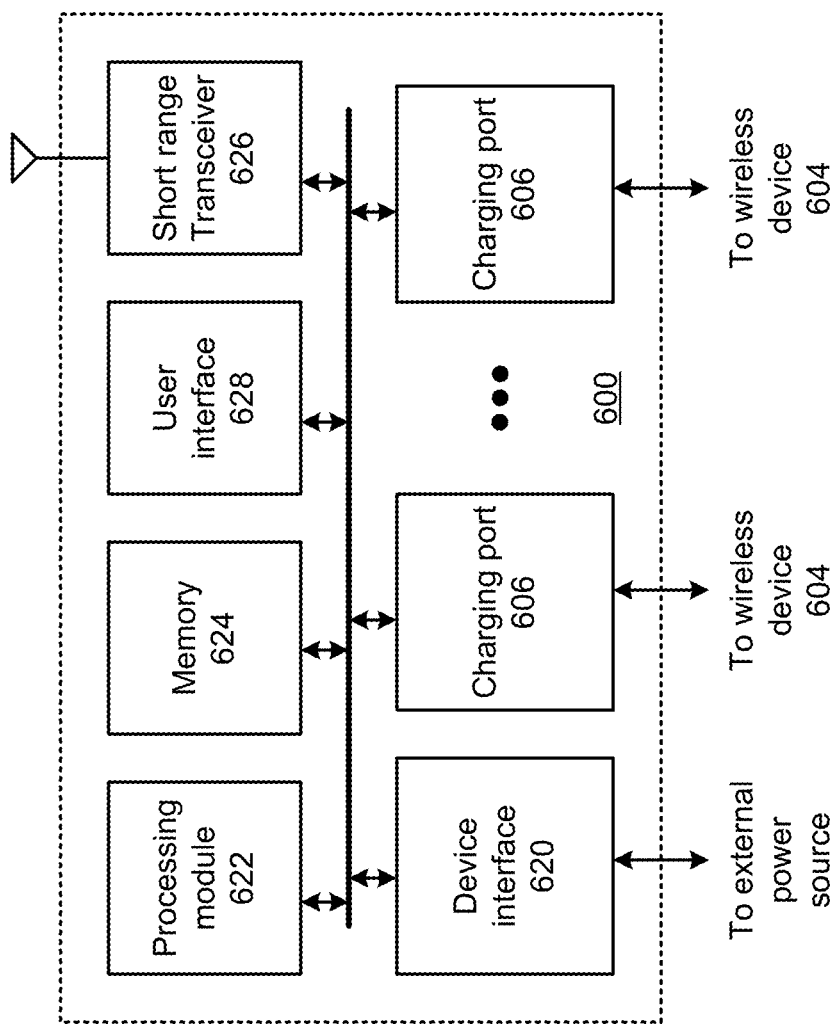
FIG. 35 presents a schematic block diagram of a charging device 600 in accordance with an embodiment of the present invention.

FIG. 35 presents a schematic block diagram of a charging device 600 in accordance with an embodiment of the present invention. Charging device 600 includes a device interface 620 for coupling power from an external power source to charging ports 606. In an embodiment of the present invention, processing module 622 controls the charging of the plurality of wireless devices 604 as a "smart charging device" to monitor the state of charge of each of the wireless devices 604 and to supply the necessary current to each wireless device 604.

In addition, processing module 622 generates charging status data for each of the plurality of wireless devices 604. The user interface 628, includes one or more lights, a display screen or other display that provides a visual indication of the charging status data for each of the plurality of wireless devices 604. The visual indication can be an indication, for example that a particular wireless device 604 is discharged, partially charged, currently charging, current battery life, fully charged, etc.

Further the charging device 600 can include a short-range wireless transceiver 626 such as short range wireless transceiver 130, 140, etc., that is pairable to the plurality of wireless devices 604 via a pairing with its corresponding short-range wireless device transceiver. In this fashion, the charging device 600 can operate in a similar fashion to adjunct device 100 described in conjunction with FIG. 13 to transmit a polling signal to a selected one of the wireless devices 604 when they are disconnected from the charging device 600 and receive status data transmitted from the corresponding wireless devices 604 in response thereto. The status data can includes a battery charge status and the user interface 628 can display an indication of the status data. In this fashion, the charging device can act as a base station to remotely monitor the charging status of selected ones of the wireless devices 604, while they are being deployed.

The processing module 622 can be implemented using a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions that are stored in memory, such as memory 624. Note that when the processing module 622 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. Further note that, the memory module 624 stores, and the processing module 622 executes, operational instructions corresponding to at least some of the steps and/or functions illustrated herein.

The memory module 624 may be a single memory device or a plurality of memory devices. Such a memory device may be a read-only memory, random access memory, volatile memory, non-volatile memory, static memory, dynamic memory, flash memory, cache memory, and/or any device that stores digital information. While the components of charging device 600 are shown as being coupled by a particular bus structure, other architectures are likewise possible that include additional data busses and/or direct connectivity between components. Charging device 600 can include additional components that are not expressly shown.

Figure 36:
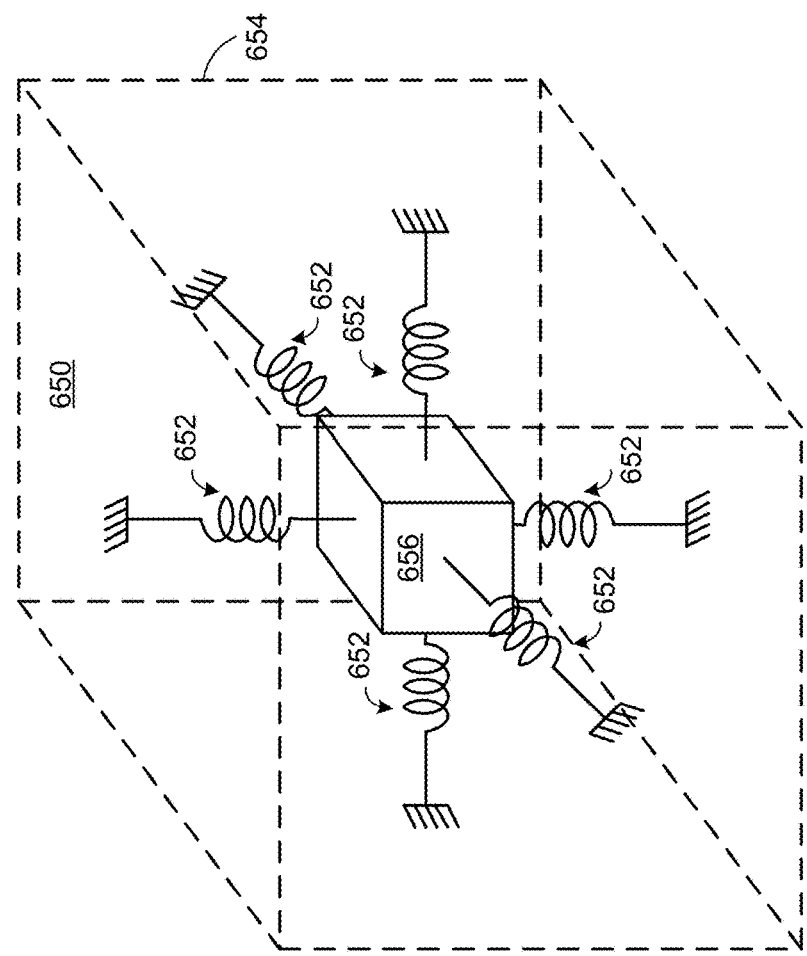
FIG. 36 presents a schematic block diagram of a charging device 600 in accordance with an embodiment of the present invention.

FIG. 36 presents a schematic block diagram of a sensor 650 in accordance with an embodiment of the present invention. Sensor 650 is constructed to be used in conjunction with any of the protective headgear 30, 31, 530, 531' to generate event data in response to an impact. In particular the sensor 650 may be constructed to more directly determine, for example, if an impact event sufficient to cause brain injury may have occurred, and more particularly if the brain and bone of the inner skull may have come into physical contact.

The sensor 650 includes a housing 654. A mass 656 is suspended in the housing 654 so as to emulate the dynamic behavior of a brain of the wearer along a plurality of axes, such as the three translational axes shown. In the configuration represented schematically a spring elements 652 serve to suspend the mass 656 from the housing 654. The spring elements can be implemented via a six-point suspension harness, elastic bands, coil springs leaf springs or other spring elements, and an elastomeric solid, a gel or other colloid, a pack of absorption particles such as elastic beads, balls, polyhedrons or other particles of the same shape, size and texture or of two or more different shapes, different sizes and/or different textures or other suspension. The sensor can include at least one damping element for damping the motion of the mass along the plurality of axes such as a fluid, a gel, and a suspension or a pack of absorption particles such as non-elastic beads, balls, polyhedrons or other particles of the same shape, size and texture or of two or more different shapes, different sizes and/or different textures. While the mass 656 and housing 654 are shown as cubic shapes, other shapes including other polyhedrons, spheres or other ellipsoids or other shapes could likewise be employed.

The sensor 650 further includes at least one sensing element for sensing the motion of the mass. For example the sensing element can include a contact sensor that generates sensor data in response to displacement of the mass along one or more axes, such as a contact or proximity sensor that measures either a contact between the mass 656 and the housing 654 or the proximity between mass 656 and the housing 654 via electrical contact, capacitive, magnetic, inductive, resistive, or conductive sensing.

The operation of sensor 650 can be discussed further in light of the following examples that set forth several optional functions, features and configurations. In one example, the mass 656 and walls of the housing 654 are constructed such that contact or proximity can be detected, where proximity correlates to severity of brain injury, and contact correlates to brain-skull contact. For example, the spring elements 652 can be implemented via elastic bands and each spring element 652 can include a strain gauge attached to the spring element to measure the deformation of the spring element. The strain gauges can be constructed by wrapping wires around the elastic bands or via other strain gauge technologies. In another configuration, the mass 656 may be suspended by six hairline wires, along x, y, and z axes, wherein the wires are configured as a three dimensional strain gauge to electrically measure the amount of stress in the system.

In another example, the capacitance between the mass 656 and the housing 654 is measured and used to determine the proximity to the mass 656 to the housing 654. In this configuration the mass 656 can be suspended via a suspension medium such as an elastomeric solid or a fluid, such as a liquid, viscous gel, semi-fluid, colloid or suspension, or the like. In this case, the suspension medium can be configured and calibrated to achieve desired mechanical properties and dynamic behaviors that mimic the skull-brain system.

In a further example, a suspension fluid may be partially or fully replaced by small solid particles, whose breakage is detectible. Particles may themselves be fluid filled, and the detection method may be to detect the presence and/or volume of fluid released by particle breakage. The particles may be glass, ceramic, or other similar materials, either spherical or elliptical in shape, whose mix and diameters may be selected in such a way as to achieve a specific empty space percentage, resulting in mechanical properties that closely resemble the shock absorbing system of the brain.

In an additional example, the mass 656 is mechanically constrained in its motion by a track, pendulum, wire, rod, magnetic field, or other means. Motion may be an arc, a circle, a line, or a defined path. Multiple masses may be configured and oriented to measure shock along lines or plains of different orientations. In particular, the mass 656 may be constrained such that a low threshold impact must occur before the mass is allowed to initially move, and a larger threshold is required for mass and container to come in contact. Constraining means may be a detent in a pathway, a breakable glass bead, glass rod, linkage, thread, wire, and the like.

In a further example, the mass 656 connected electrically via a wire could be suspended in a gas, a liquid or compressible solid, where mass and suspension material have distinctly different dielectric constants. The housing 656 could be etched with some metal pads and the proximity to the mass 656 to each of the metal pads on the sphere could be detected by a simple circuit measuring the change in capacitance between the pads and the mass. In another configuration, the mass 656 could be fully suspended in an enclosed sphere without a wire attached to the mass. The medium and mass would have distinctly different dielectric constants, one low and the other high. In this configuration, pads are etched on the surface of the enclosing sphere and a circuit is constructed to detect the capacitance between pairs of pads. As the mass moves within the sphere due to impacts, the capacitance between pairs of pads will change due to the changing dielectric constant between them.

The sensor 656 may be attached or built into a protective helmet, employed in a wireless device 120, 121 or 531' or a device 531 that generates event data 16 when a threshold event occurs, and further to inform medical personnel of the extent or nature of an injury. As previously discussed, event data 16 can be used for other purposes including generating simulation data or further used in research studies to improve the design of protective equipment/systems, including vehicle crash studies.

Figure 37:
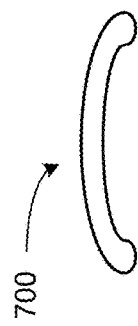
FIG. 37 presents a pictorial representation of a cross section of a bladder 700 in accordance with an embodiment of the present invention.

FIG. 37 presents a pictorial representation of a cross section of a bladder 700 in accordance with an embodiment of the present invention. In particular, a bladder 700 is shown for use in a protective helmet or other protective headgear that includes an outer shell. A bladder 700 is coupled to the outer shell and provides shock absorption in at least one zone of protection. The bladder 700 either holds an absorption pack that contains a plurality of absorption particles or a fluid and has a relief valve for relieving pressure on the bladder when the pressure on the bladder is greater than a pressure threshold. The goal of this bladder 700 is to mitigate the effects of an impact to the head. This can be accomplished by dissipating the shock over as large a surface area as possible, and as large a timespan as possible. Current designs use pads, air cells, liquid filled cells, etc., inside a shell structure to accomplish these goals.

In an embodiment of the present invention, the bladder is a liquid filled cell that is pressure limited to spread shocks over a larger timespan, and reducing the likelihood of concussion or other brain injury. Further details regarding the bladder 700, its use in conjunction with a protective helmet or other protective headgear, and how it is filled, including several optional functions and features, are discussed in conjunction with FIGS. 38-42.

Figure 38:
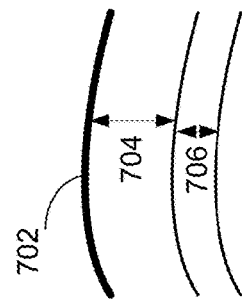
FIG. 38 presents a pictorial representation of a cross section of a helmet in accordance with an embodiment of the present invention.

FIG. 38 presents a pictorial representation of a cross section of a helmet in accordance with an embodiment of the present invention. A portion of the helmet is shown that includes an outer shell 702 and multiple layers 704 and 706. While two layers are shown, three or more layers can be implemented in a sandwiched or layered design. Each of the layers can be implemented via the bladder 700, and other shock absorbing materials, such foams, air bladders, and other materials.

In an embodiment of the present invention, one of the layers is implemented via at least one inflatable element that is selectively inflatable to improve the fit between the protective helmet and a wearer of the protective helmet and to establish an initial pressurization of the system, improving the ability of fluid-filled bladders to more effectively spread load over larger surface areas of the head. While a portion of a helmet is shown, multiple bladders 700 may be employed in different portions of the helmet or other protective headgear, forming multiple zones of protection. In addition, multiple bladders or other fluid chambers can be connected via connection tubes, pressure valves or other fluid flow channels to redistribute fluid in response to an impact event. For example, front and rear bladders connected in this fashion can transfer impact force from a rear impact event to the front bladder to transfer some of the impact force.

Figure 39:
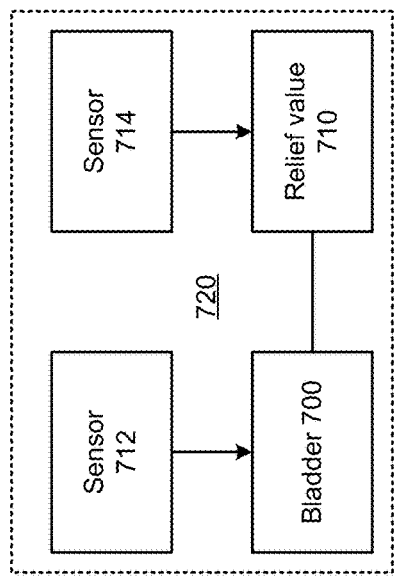
FIG. 39 presents a schematic block diagram of protective headgear in accordance with an embodiment of the present invention.

FIG. 39 presents a schematic block diagram of protective headgear in accordance with an embodiment of the present invention. Protective headgear 720 is presented that can be implemented to optionally generate event data 16 or other event data in conjunction with any of the previous designs. The protective headgear 720 includes a bladder 700 that is coupled to a relief valve 710 that releases fluid from the at least one bladder to either the exterior to the protective headgear or from one bladder to another bladder, such as an adjacent zone or to a reservoir. The pressure relief valve 710 expels fluid once a threshold pressure has been exceeded, maintaining a constant pressure for a controlled period of time, mitigating the effect of an excessive shock event—in effect, acting as a hydraulic shock absorber.

In an embodiment of the present invention, the release of fluid to the exterior of the protective headgear or to a reservoir, such as reservoir equipped with a viewing window can be used to visually inform an observer that an excess pressure event has occurred or otherwise to the exterior of the bladder 700. The fluid can contain a dye to enhance the visibility of the fluid on the exterior of the protective headgear or in the reservoir.

Protective headgear 720 optionally includes one or more sensors, such as sensors 712 and 714. Sensor 714 monitors the relief valve 710 that generates sensor data in response to a release of pressure by the relief valve 710, that can be used as event data or can be used to generate event data such as event data 16. In addition or in the alternative, sensor 712 monitors for a contact or the proximity between walls of the bladder via magnetic, capacitive, inductive, resistive, or conductive means, or via a pressure sensor that generates sensor data in response to a shock event, such as event data 16 or other event data. While a single sensor 712 is shown, multiple sensors 712 can be distributed within the bladder 700 to generate data that indicates the location and/or direction of an impact event or that otherwise generates sensor data that represents a pressure profile of an impact event. Further, multiple sensors 712 can be in embodiments where multiple bladders 700 are employed in different portions of the helmet or other protective headgear. For example, when multiple bladders 700 are connected via connection tubes, pressure valves or other fluid flow channels to redistribute fluid in response to an impact event, multiple sensors 712 can be included to monitor multiple zones of protection.

The bladder 700 can be filled with a fluid fill material, such as a liquid, a gel or other colloid, a suspension or any of a variety of low durometer elastomeric materials. As will be discussed further in conjunction with FIGS. 40-42, the bladder 700 can hold fluid fill material composed of rigid material mixes of absorption particles, such as glass or ceramic beads, spherical or elliptical in shape, with various mechanical properties and/or of various geometries, which are chosen in specific mixes/ratios to create specific target air-space percentages in a mix and to calibrate the mechanical properties to achieve desired optimal mechanical and shock absorbing characteristics. When bladder 700 holds a rigid material mixes of absorption particles, interstitial areas can be filled with a liquid or a gas. The pressure relief valve 710 and sensor 714 may or may not be included.

Figure 40:
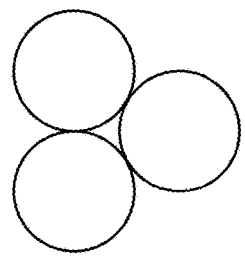
FIG. 40 presents a pictorial representation of a cross section of absorption particles accordance with an embodiment of the present invention.

FIG. 40 presents a pictorial representation of a cross section of absorption particles accordance with an embodiment of the present invention. As discussed above, a bladder, such as bladder 700 used in conjunction with protective headgear, such as protective headgear 720 or other protective headgear can hold an absorption pack containing a plurality of absorption particles. The absorption particles can form a solid mixture made of otherwise rigid materials, that creates unique shock absorbing characteristics by virtue interstitial interactions. In the example shown, spherical particles of a single size (a mono-mix) are used.

Unlike foam materials, which transfer shock when maximum compression of the material is achieved, glass/ceramic mixes provide an extra level of protection. When the elastic capacity of the mix is exceeded, the rigid materials mechanically fail, relieving local stress preventing chain-reaction break-downs, and thus transfer the shock at a threshold value until a substantial portion of the mix material has failed.

In an embodiment of the present invention, the absorption particles are implemented via frangible beads. When such a threshold-exceeding event has occurred, the protective capacity of the system is compromised, the beads begin to break and compromised components must be replaced. Further, when such a failure has occurred, the breakage of the beads can be detected electronically via a proximity or contact sensor. In a further embodiment hollow frangible beads are employed that are filled with a colored die that is released either to a reservoir with a viewing window or externally to the protective headgear to allow for visual observation.

Solid mixtures may be blended that contain both rigid materials, such as glass/ceramic, and elastomeric spheres of various sizes, shapes, frictional characteristics and mixture balances between rigid and plastic material—again to achieve desired mechanical and dynamic properties.

Figure 41:
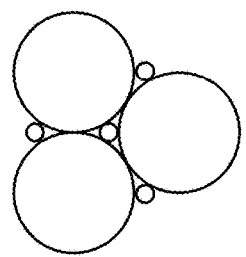
FIG. 41 presents a pictorial representation of a cross section of absorption particles accordance with an embodiment of the present invention.

FIG. 41 presents a pictorial representation of a cross section of absorption particles accordance with an embodiment of the present invention. In the embodiment shown, absorption particles of two sizes, (a binary mix), is presented. Different frictional characteristics can be implemented by particle finishes that vary from smooth to rough. While a spherical shape is shown, addition shapes from spherical to non-spherical, regular, to even irregular can also be implemented. Frictional interactions and even interference interactions among particles will contribute to the mix's bulk physical properties. In a binary mix such as the mix shown, two very different materials can be used. For example, a first bead type can be implemented with a ceramic bead which is very rigid, and a second bead type can be implemented via a polymer material which is very springy, and so forth.

Figure 42:
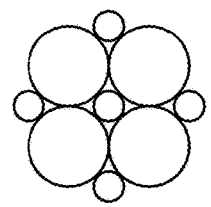
FIG. 42 presents a pictorial representation of a cross section of absorption particles accordance with an embodiment of the present invention.

FIG. 42 presents a pictorial representation of a cross section of absorption particles accordance with an embodiment of the present invention. A binary mix of absorption particles is shown that implements a different stacking configuration from the example presented in conjunction with FIG. 41. Stacking configurations are controlled by particle sizes, shapes, pressure and so forth. Typical configurations would be pyramidal or cubic, but one could easily imagine more complex structures, not unlike what might be seen in crystal lattice structures. Implementing particle sizes that produce one stacking configuration over another allow greater control over the physical properties of the mix.

Figure 43:
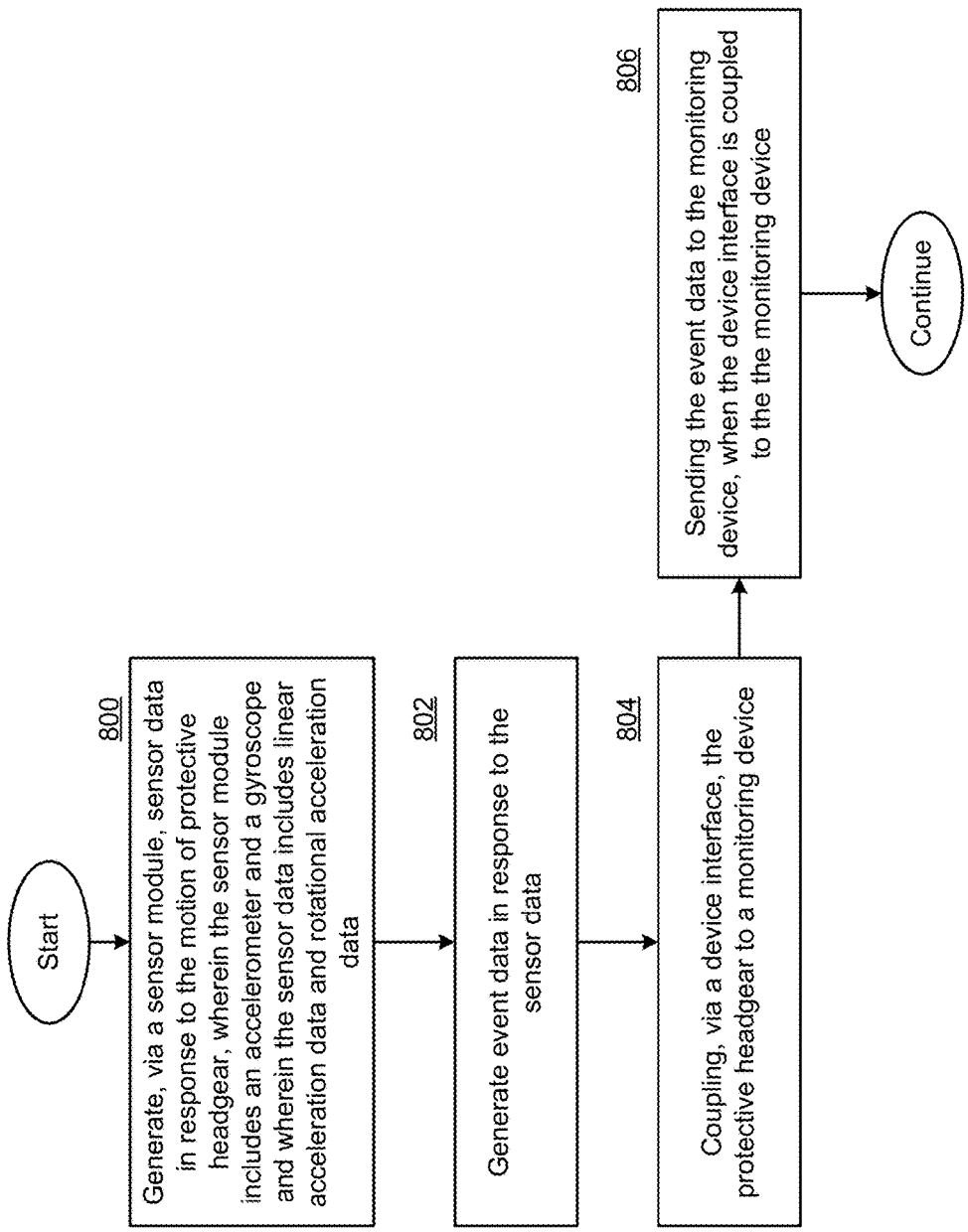
FIG. 43 presents a flowchart representation of a method in accordance with an embodiment of the present invention.

FIG. 43 presents a flowchart representation of a method in accordance with an embodiment of the present invention. In particular, a method is presented for use in conjunction with any of the functions and features described in conjunction with FIGS. 1-42. In step 800, sensor data is generating, via a sensor module, in response to an impact to protective headgear, wherein the sensor module includes an accelerometer and a gyroscope and wherein the sensor data includes linear acceleration data and rotational velocity data. In step 802, event data is generated in response to the sensor data. In step 804, the protective headgear is coupled, via device interface to a monitoring device. In step 806, the event data is sent to the monitoring device, when the device interface is coupled to the monitoring device.

In an embodiment of the present invention, the monitoring device is coupled via a standardized cable having a plug that mates with a jack of the device interface. The standardized cable can be a universal serial bus cable.

In an embodiment of the present invention, the accelerometer responds to acceleration of the protective headgear along a plurality of axes and wherein the linear acceleration data indicates the acceleration of the protective headgear along the plurality of axes. The gyroscope can respond to velocity of the protective headgear along a plurality of axes and wherein the rotational velocity data indicates the velocity of the protective headgear along the plurality of axes.

The protective headgear can include a football helmet, a headband, a mouth guard other protective headgear or component thereof or other protective article. The monitoring device can be a handheld communication device, a personal computer or other device.

While much of the description above includes the use of an adjunct device 100 and handheld communication device 110, the functionality of adjunct device 100 can be built into the handheld device 100 in order to facilitate communication with protective headgear.

While the description above has set forth several different modes of operation, the devices described here may simultaneously be in two or more of these modes, unless, by their nature, these modes necessarily cannot be implemented simultaneously. While the foregoing description includes the description of many different embodiments and implementations, the functions and features of these implementations and embodiments can be combined in additional embodiments of the present invention not expressly disclosed by any single implementation or embodiment, yet nevertheless understood by one skilled in the art when presented this disclosure.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "operably coupled to", "coupled to", and/or "coupling" includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

As may also be used herein, the terms "processing module", "processing circuit", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

The present invention has been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of the various embodiments of the present invention. A module includes a processing module, a functional block, hardware, and/or software stored on memory for performing one or more functions as may be described herein. Note that, if the module is implemented via hardware, the hardware may operate independently and/or in conjunction software and/or firmware. As used herein, a module may contain one or more sub-modules, each of which may be one or more modules.

While particular combinations of various functions and features of the present invention have been expressly described herein, other combinations of these features and functions are likewise possible. The present invention is not limited by the particular examples disclosed herein and expressly incorporates these other combinations.

Thus, there has been described herein an apparatus and method, as well as several embodiments including a preferred embodiment. Various embodiments of the present invention herein-described have features that distinguish the present invention from the prior art.

It will be apparent to those skilled in the art that the disclosed invention may be modified in numerous ways and may assume many embodiments other than the preferred forms specifically set out and described above. Accordingly, it is intended by the appended claims to cover all modifications of the invention which fall within the true spirit and scope of the invention.

What is claimed is:

1. A system comprising:
  protective headgear;
  a sensor module, coupled to the protective headgear that generates sensor data in response to an impact to the protective headgear, wherein the sensor module includes an accelerometer and a gyroscope and wherein the sensor data includes linear acceleration data and rotational velocity data;
  a device processing module, coupled to the sensor module, that generates power diffusion data in response to the sensor data, wherein the power diffusion data indicates a mass independent power diffusion caused by the impact to the protective headgear, and wherein the device processing module further generates event data that includes the power diffusion data; and
  a device interface, coupled to the sensor module and the device processing module, that is coupleable to a monitoring device and that sends the event data to the monitoring device when the device interface is coupled to the monitoring device.

2. The system of claim 1 wherein the device interface includes a jack that is coupleable to the monitoring device via a standardized cable having a plug that mates with the jack.

3. The system of claim 2 wherein the standardized cable is a universal serial bus cable.

4. The system of claim 1 wherein the accelerometer responds to acceleration of the protective headgear along a plurality of axes and wherein the linear acceleration data indicates the acceleration of the protective headgear along the plurality of axes.

5. The system of claim 1 wherein the gyroscope responds to velocity of the protective headgear along a plurality of axes and wherein the rotational velocity data indicates the velocity of the protective headgear along the plurality of axes.

6. The system of claim 1 wherein the protective headgear includes a football helmet.

7. The system of claim 1 wherein the protective headgear includes a mouth guard.

8. The system of claim 1 wherein the monitoring device includes a handheld communication device.

9. The system of claim 1 wherein the monitoring device includes a personal computer.

10. The system of claim 1 wherein the sensor module includes a plurality of individual sensors placed at different points on the protective headgear, wherein the plurality of individual sensors includes the accelerometer and the gyroscope.

11. The system of claim 1 wherein the device interface includes a one connector interface.

12. The system of claim 11 wherein the one connector interface includes a contact pad.

13. The system of claim 11 wherein the device interface detects coupling to the monitoring device and the device interface initiates transmission of the event data via the one connector interface to the monitoring device in response to the detection of the coupling by the monitoring device.

14. A method for use in a system for monitoring protective headgear, the method comprising:
  generating, via a sensor module, sensor data in response to an impact to the protective headgear, wherein the sensor module includes an accelerometer and a gyroscope and wherein the sensor data includes linear acceleration data and rotational velocity data;
  generating power diffusion data in response to the sensor data, wherein the power diffusion data indicates a mass independent power diffusion caused by the impact to the protective headgear;
  generating event data that includes the power diffusion;
  coupling, via a device interface, the protective headgear to a monitoring device; and
  sending the event data to the monitoring device, when the device interface is coupled to the monitoring device.

15. The method of claim 14 wherein the coupling to the monitoring device is via a standardized cable having a plug that mates with a jack of the device interface.

16. The method of claim 14 wherein the accelerometer responds to acceleration of the protective headgear along a plurality of axes and wherein the linear acceleration data indicates the acceleration of the protective headgear along the plurality of axes.

17. The method of claim 14 wherein the gyroscope responds to velocity of the protective headgear along a plurality of axes and wherein the rotational velocity data indicates the velocity of the protective headgear along the plurality of axes.

18. The method of claim 14 wherein the protective headgear includes one of: a football helmet, a mouthguard, a hard hat, a military helmet, a chin strap, an ear piece and a skull cap.

19. The method of claim 14 wherein the monitoring device includes a handheld communication device.

20. The method of claim 14 wherein the monitoring device includes a personal computer.

* * * * *